United States Patent
Cui et al.

(10) Patent No.: US 12,357,965 B2
(45) Date of Patent: Jul. 15, 2025

(54) SUPRAMOLECULAR FILAMENTOUS ASSEMBLIES FOR PROTEIN PURIFICATION

(71) Applicants: The Johns Hopkins University, Baltimore, MD (US); Bristol-Myers Squibb Company, Princeton, NJ (US)

(72) Inventors: Honggang Cui, Lutherville, MD (US); Yi Li, Baltimore, MD (US); Lye Lin Lock, Maynard, MA (US); XuanKuo Xu, Boxborough, MA (US); Zhengjian Li, Sudbury, MA (US)

(73) Assignees: The Johns Hopkins University, Baltimore, MD (US); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 18/460,024

(22) Filed: Sep. 1, 2023

(65) Prior Publication Data
US 2024/0082816 A1    Mar. 14, 2024

Related U.S. Application Data

(62) Division of application No. 16/639,763, filed as application No. PCT/US2018/046924 on Aug. 17, 2018, now Pat. No. 11,745,165.

(60) Provisional application No. 62/547,256, filed on Aug. 18, 2017.

(51) Int. Cl.
| | |
|---|---|
| *B01J 20/24* | (2006.01) |
| *B01D 15/38* | (2006.01) |
| *B01J 20/28* | (2006.01) |
| *B01J 20/34* | (2006.01) |
| *C07K 1/22* | (2006.01) |
| *C07K 7/08* | (2006.01) |
| *C07K 14/31* | (2006.01) |
| *C07K 16/06* | (2006.01) |

(52) U.S. Cl.
CPC .......... *B01J 20/24* (2013.01); *B01D 15/3809* (2013.01); *B01J 20/28023* (2013.01); *B01J 20/3425* (2013.01); *B01J 20/3475* (2013.01); *C07K 1/22* (2013.01); *C07K 7/08* (2013.01); *C07K 14/31* (2013.01); *C07K 16/065* (2013.01)

(58) Field of Classification Search
CPC ................ A61K 47/542; A61K 47/543; B01D 15/3804; B01D 15/3809; B01J 20/28023; C07K 1/22; C07K 2/00; C07K 4/00; C07K 5/1005–101
See application file for complete search history.

(56) References Cited

U.S. PATENT DOCUMENTS

| | | |
|---|---|---|
| 5,223,409 A | 6/1993 | Ladner et al. |
| 5,403,484 A | 4/1995 | Ladner et al. |
| 5,427,908 A | 6/1995 | Dower et al. |
| 5,476,996 A | 12/1995 | Wilson et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,698 A | 11/1996 | Ladner et al. |
| 5,580,717 A | 12/1996 | Dower et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,698,767 A | 12/1997 | Wilson et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,885,793 A | 3/1999 | Griffiths et al. |
| 5,939,598 A | 8/1999 | Kucherlapati et al. |
| 5,969,108 A | 10/1999 | McCafferty et al. |
| 6,013,763 A | 1/2000 | Braisted et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,172,197 B1 | 1/2001 | McCafferty et al. |
| 6,197,927 B1 | 3/2001 | Braisted |
| 6,521,404 B1 | 2/2003 | Griffiths et al. |
| 6,544,731 B1 | 4/2003 | Griffiths et al. |

(Continued)

FOREIGN PATENT DOCUMENTS

| | | |
|---|---|---|
| JP | 2020512385 | 4/2020 |
| WO | WO 199203918 | 3/1992 |

(Continued)

OTHER PUBLICATIONS

Altunbas et al., Encapsulation of curcumin in self-assembling peptide hydrogels as injectable drug delivery vehicles. Biomaterials 2011, 32 (25), 5906-14.

(Continued)

*Primary Examiner* — Christina Bradley
(74) *Attorney, Agent, or Firm* — Casimir Jones, S.C.; Thomas A. Isenbarger

(57) ABSTRACT

The present invention provide novel immunofiber compositions for protein or peptide purification and simple and cost-efficient methods and systems using these compositions. In some embodiments, the immunofibers comprise a customized Z-33 peptide derived from *Staphylococcus aureus* Protein A which is used to construct immunoamphiphile molecules that assemble into immunofibers in aqueous solution with bioactive epitopes on the surface and have peptide or protein binding ability.

12 Claims, 20 Drawing Sheets

Figures 1A, 1B, 1C:
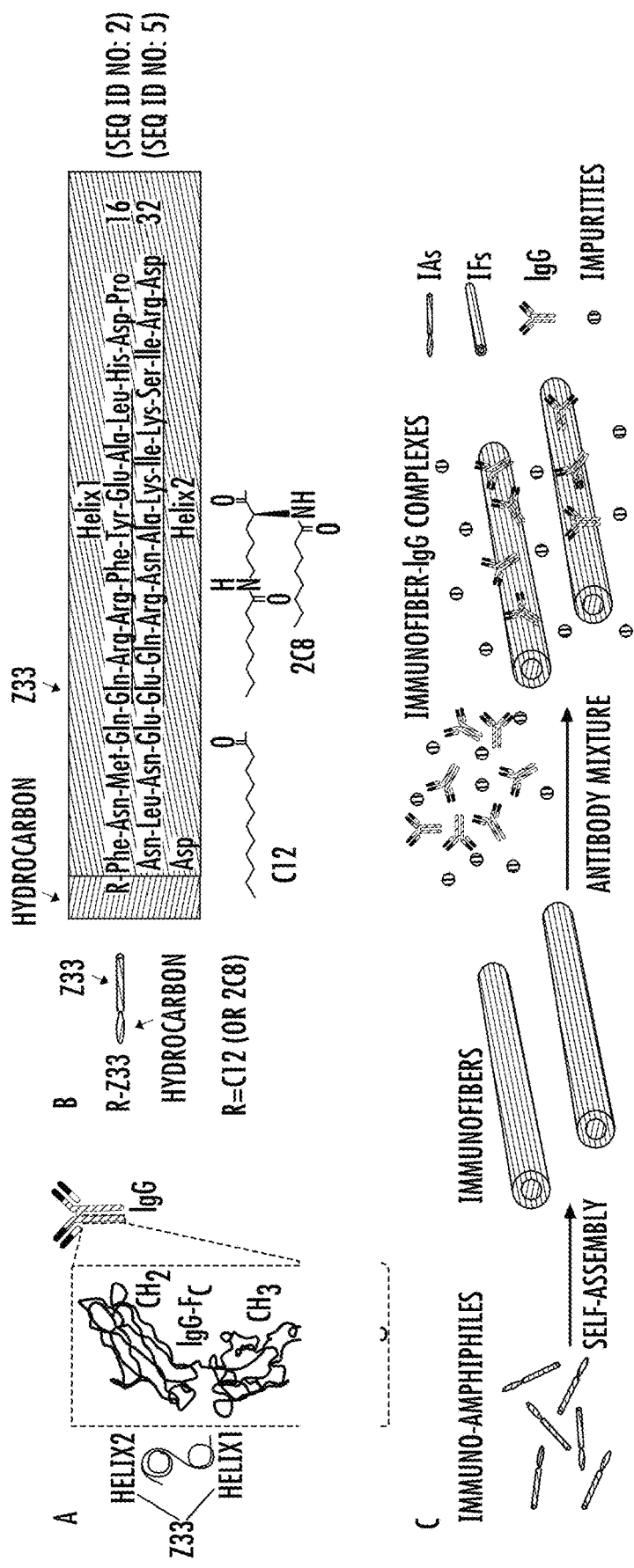

Specification includes a Sequence Listing.

(56) References Cited

U.S. PATENT DOCUMENTS

| | | | |
|---|---|---|---|
| 6,555,313 B1 | 4/2003 | Griffiths et al. | |
| 6,582,915 B1 | 6/2003 | Griffiths et al. | |
| 6,593,081 B1 | 7/2003 | Griffiths et al. | |
| 6,641,816 B1 * | 11/2003 | Chevalier | A61K 39/145 424/191.1 |
| 8,076,295 B2 | 12/2011 | Hulvat | |
| 9,650,421 B2 | 5/2017 | Stupp | |
| 11,359,005 B2 | 6/2022 | Cui et al. | |
| 11,745,165 B2 * | 9/2023 | Cui | C07K 14/31 530/387.1 |
| 2003/0175731 A1 * | 9/2003 | Fearon | A61P 31/04 435/6.1 |
| 2009/0098652 A1 | 4/2009 | Stupp et al. | |
| 2012/0294902 A1 * | 11/2012 | Stupp | C07K 2/00 530/300 |
| 2013/0101628 A1 | 4/2013 | Webber et al. | |
| 2018/0221513 A1 * | 8/2018 | Preslar | A61K 51/088 |

FOREIGN PATENT DOCUMENTS

| | | |
|---|---|---|
| WO | WO 199312227 | 6/1993 |
| WO | WO 199425585 | 11/1994 |
| WO | WO 199713852 | 4/1997 |
| WO | WO 199824884 | 6/1998 |
| WO | WO 199945962 | 9/1999 |
| WO | WO 200114424 | 3/2001 |
| WO | WO 2002243478 | 6/2002 |
| WO | WO 2017123585 | 7/2017 |
| WO | WO 2018/183417 | 10/2018 |

OTHER PUBLICATIONS

Arslan, et al., Bioactive supramolecular peptide nanofibers for regenerative medicine. Advanced healthcare materials 2014, 3, (9), 1357-1376.

Bellomo, et al., Stimuli-responsive polypeptide vesicles by conformation-specific assembly. Nat Mater 2004, 3, (4), 244-8.

Benzinger, et al., Propagating structure of Alzheimer's beta-amyloid (10-35) is parallel beta-sheet with residues in exact register. Proc. Natl. Acad. Sci. U. S. A. 1998, 95, (23), 13407-13412.

Biancalana, et al., Molecular mechanism of Thioflavin-T binding to amyloid fibrils. Biochim Biophys Acta 2010, 1804, (7), 1405-12.

Bitton, et al., Self-assembly of model DNA-binding peptide amphiphiles. Langmuir 2005, 21, (25), 11888-11895.

Black et al., Self-Assembled Peptide Amphiphile Micelles Containing a Cytotoxic T-Cell Epitope Promote a Protective Immune Response In Vivo. Adv Mater 2012, 24 (28), 3845-3849.

Boutelje et al., Human immunodeficiency viral protease is catalytically active as a fusion protein: characterization of the fusion and native enzymes produced in *Escherichia coli*. Archives of biochemistry and biophysics 1990, 283 (1), 141-149.

Braisted, et al., Minimizing a binding domain from protein A. Proceedings of the National Academy of Sciences 1996, 93, (12), 5688-5692.

Cheetham, et al., Supramolecular nanostructures formed by anticancer drug assembly. J Am Chem Soc 2013, 135, (8), 2907-10.

Chen et al. Immunoglobulin gene rearrangement in B cell deficient mice generated by targeted deletion of the JH locus (1993) International Immunology 5: 647-656.

Chen et al., B cell development in mice that lack one or both immunoglobulin kappa light chain genes. (1993) EMBO J. 12: 821-830.

Choi et al., Transgenic mice containing a human heavy chain immunoglobulin gene fragment cloned in a yeast artificial chromosome (1993) Nature Genetics 4:117-123.

Chothia, et al., Helix to helix packing in proteins. J. Mol. Biol. 1981, 145, (1), 215-250.

Chow et al., Self-assembling nanostructures to deliver angiogenic factors to pancreatic islets. Biomaterials 2010, 31 (24), 6154-61.

Chu-Kung, et al., Effect of Fatty Acid Conjugation on Antimicrobial Peptide Activity; DTIC Document: 2004.

Clackson et al., Making antibody fragments using phage display libraries., Nature 352:624-628 (1991).

Cuatrecasas., Protein purification by affinity chromatography. J. Biol. Chem 1970, 245 (12), 3050.

Cui et al., Amino Acid Sequence in Constitutionally Isomeric Tetrapeptide Amphiphiles Dictates Architecture of One-Dimensional Nanostructures. Journal of the American Chemical Society 2014, 136 (35), 12461-12468.

Cui, et al., Self-assembly of peptide amphiphiles: from molecules to nanostructures to biomaterials. Biopolymers 2010, 94, (1), 1-18.

Deisenhofer., Crystallographic refinement and atomic models of a human Fc fragment and its complex with fragment B of protein A from *Staphylococcus aureus* at 2.9-and 2.8-. ANG resolution. Biochemistry 1981, 20 (9), 2361-2370.

Demers et al., Binding mechanism of an SH3 domain studied by NMR and ITC. Journal of the American Chemical Society 2009, 131 (12), 4355-4367.

Deng et al. Self-assembly of Peptide-Amphiphile C12-Abeta (I 1-17) into Nanofibrils. Journal of Physical Chemistry B. 2009, vol. 113, No. 25, pp. 8539-8544. (Year: 2009).

Ecker et al., The therapeutic monoclonal antibody market. MAbs 2015, 7 (1), 9-14.

Eisen et al., Variations in Affinities of Antibodies during the Immune Response*. Biochemistry 1964, 3 (7), 996-1008.

Fishwild et al. High-avidity human IgG kappa monoclonal antibodies from a novel strain of minilocus transgenic mice. (1996) Nature Biotechnology 14: 845-851.

Forns, et al., Induction of protein-like molecular architecture by monoalkyl hydrocarbon chains. Biopolymers 2000, 54, (7), 531-546.

Forsgren, et al., "Protein A" from *S. aureus*. I. Pseudo-immune reaction with human gamma-globulin. J. Immunol. 1966, 97, (6), 822-827.

Freire et al., Characterisation of ligand binding by calorimetry. In Biophysical Approaches Determining Ligand Binding to Biomolecular Targets, 2011; pp. 275-299.

Gazit, A possible role for π-stacking in the self-assembly of amyloid fibrils. The FASEB Journal 2002, 16, (1), 77-83.

Gong, Y., et al., "Development of the Double Cyclic Peptide Ligand for Antibody Purification and Protein Detection", Bioconjugate Chem (2016) 27, 1569-1573.

Greenfield, et al., Computed circular dichroism spectra for the evaluation of protein conformation. Biochemistry 1969, 8, (10), 4108-4116.

Haines-Butterick, et al., Controlling hydrogelation kinetics by peptide design for three-dimensional encapsulation and injectable delivery of cells. Proceedings of the National Academy of Sciences 2007, 104, (19), 7791-7796.

Han, et al., Bioinspired self-assembled peptide nanofibers with thermostable multivalent alphahelices. Biomacromolecules 2013, 14, (5), 1594-9.

Handlogten et al., Nonchromatographic affinity precipitation method for the purification of bivalently active pharmaceutical antibodies from biological fluids. Analytical chemistry 2013, 85 (10), 5271-5278.

Hartgerink, et al., Self-assembly and mineralization of peptide-amphiphile nanofibers. Science 2001, 294, (5547), 1684-1688.

Hassouneh et al., Elastin-like polypeptides as a purification tag for recombinant proteins. Curr Protoc Protein Sci 2010, Chapter 6, Unit 611.

Henchey, et al., Contemporary strategies for the stabilization of peptides in the α-helical conformation. Current opinion in chemical biology 2008, 12, (6), 692-697.

Hober et al., Protein A chromatography for antibody purification. J Chromatogr B Analyt Technol Biomed Life Sci 2007, 848 (1), 40-7.

Hol, The role of the α-helix dipole in protein function and structure. Progress in biophysics and molecular biology 1985, 45, (3), 149-195.

Hu et al., Spatiotemporal control of the creation and immolation of peptide assemblies. Coordination Chemistry Reviews 2016, 320, 2-17.

Hu, et al., Electrostatic-Driven Lamination and Untwisting of beta-Sheet Assemblies. ACS Nano 2016, 10, (1), 880-8.

(56) References Cited

OTHER PUBLICATIONS

Hudson, et al., The thioflavin T fluorescence assay for amyloid fibril detection can be biased by the presence of exogenous compounds. FEBS J 2009, 276, (20), 5960-72.
Huse et al., Purification of antibodies by affinity chromatography. Journal of biochemical and biophysical methods 2002, 51 (3), 217-231.
Huttl, C. et al. Self-assembled peptide amphiphiles function as multivalent binder with increased hemagglutinin affinity. BMC Biotechnol. Jun. 18, 2013;13:51.
Jaenicke, A rapid micromethod for the determination of nitrogen and phosphate in biological material., Anal. Biochem., 61.2 (1974): 623-627.
Jones et al., Replacing the complementarity-determining regions in a human antibody with those from a mouse Nature 321:522-525 (1986).
Karcher, S., et al., "Molecular Biology A Project Approach" Academ Press (1995) pp. 79-81.
Kawashima et al., EpCAM- and EGFR-targeted selective gene therapy for biliary cancers using Z33-fiber modified adenovirus. Int J Cancer 2011, 129 (5), 1244-53.
Kenan, D., et al., "Peptide-PEG Amphiphiles as Cytophobic Coatings for Mammalian and Bacterial Cells" Chemistry & Biology 13, 695-700, Jul. 2006 DOI 10.1016/j.chembiol.2006.06.013.
Kickhoefer et al., Targeting vault nanoparticles to specific cell surface receptors. Acs Nano 2008, 3 (1), 27-36.
Kohler et al., Continuous cultures of fused cells secreting antibody of predefined specificity., Nature 256:495 (1975).
Kokkoli, et al., Self-assembly and applications of biomimetic and bioactive peptide-amphiphiles. Soft Matter 2006, 2, (12), 1015.
Korevaar, et al., Pathway selection in peptide amphiphile assembly. J Am Chem Soc 2014, 136, (24), 8540-3.
Koutsopoulos et al., Two-layered injectable self-assembling peptide scaffold hydrogels for long-term sustained release of human antibodies. J Control Release 2012, 160 (3), 451-8.
Leung, et al., Molecular Crystallization Controlled by pH Regulates Mesoscopic Membrane Morphology. ACS Nano 2012, 6, (12), 10901-10909.
Li, Y., et al., "Bioinspired supramolecular engineering of self-assembling immunofibers for high affinity binding of mmunoglobulin G" Biomaterials 178 (2018) 448-457.
Lin, et al., Supramolecular filaments containing a fixed 41% paclitaxel loading. Chem Commun (Camb) 2013, 49, (43), 4968-70.
Lin, et al., Supramolecular Polymers Formed by ABC Miktoarm Star Peptides. ACS Macro Lett 2013, 2, (12), 1088-1094.
Lock et al., Tuning Cellular Uptake of Molecular Probes by Rational Design of Their Assembly into Supramolecular Nanoprobes. Journal of the American Chemical Society 2016, 138 (10), 3533-3540.
Lock, et al., One-Component Supramolecular Filament Hydrogels as Theranostic Label-Free Magnetic Resonance Imaging Agents. ACS Nano 2017, 11, (1), 797-805.
Lock, et al., Self-assembly of natural and synthetic drug amphiphiles into discrete supramolecular nanostructures. Faraday Discussions 2013, 166, 285.
Lockwood, et al., Acylation of SC4 dodecapeptide increases bactericidal potency against Grampositive bacteria, including drug-resistant strains. Biochemical Journal 2004, 378, (1), 93-103.
Low et al., Future of antibody purification. J Chromatogr B Analyt Technol Biomed Life Sci 2007, 848 (1), 48-63.
Lowik, et al., Tuning secondary structure and self-assembly of amphiphilic peptides. Langmuir 2005, 21, (2), 524-526.
Luan et al. Peptide amphiphiles with multifunctional fragments promoting cellular uptake and endosomal escape as efficient gene vectors. Journal of Materials Chemistry B. 2015, vol. 3, pp. 1068-1078. (Year: 2015).
Lund et al., Exploring variation in binding of Protein A and Protein G to immunoglobulin type G by isothermal titration calorimetry. J Mol Recognit 2011, 24 (6), 945-52.
Luo, et al., Structural dynamic of a self-assembling peptide d-EAK16 made of only D-amino acids. PLoS One 2008, 3, (5), e2364.

Ma et al., Building nanostructures with drugs. Nano Today 2016, 11 (1), 13-30.
Madan et al., ELP-z and ELP-zz capturing scaffolds for the purification of immunoglobulins by affinity precipitation. J Biotechnol 2013, 163 (1), 10-6.
Marks et al., By-passing immunization: human antibodies from V-gene libraries displayed on phage J. Mol. Biol. 222:581-597 (1991).
Marqusee, et al., Unusually stable helix formation in short alanine-based peptides. Proceedings of the National Academy of Sciences 1989, 86, (14), 5286-5290.
Meng, et al., Nanostructures from the self-assembly of alpha-helical peptide amphiphiles. J Pept Sci 2014, 20, (3), 223-8.
Moks et al., Staphylococcal protein A consists of five IgG-binding domains. European Journal of Biochemistry 1986, 156 (3), 637-643.
Morrison et al., Chimeric human antibody molecules: mouse antigen-binding domains with human constant region domains Proc. Natl. Acad. Sci. USA 81:6851-6855 (1984).
Moyer et al., pH and Amphiphilic Structure Direct Supramolecular Behavior in Biofunctional Assemblies. Journal of the American Chemical Society 2014, 136 (42), 14746-14752.
Neame, et al., Inexpensive liquid scintillation counting of aqueous samples. Anal Biochem 1974, 57, (2), 623-627.
Nelson, et al., Stabilization of the ribonuclease S-peptide α-helix by trifluoroethanol. Proteins: Structure, Function, and Bioinformatics 1986, 1, (3), 211-217.
Nilsson et al., A synthetic IgG-binding domain based on staphylococcal protein A. Protein engineering 1987, 1 (2), 107-113.
Nowak, et al., Rapidly recovering hydrogel scaffolds from self-assembling diblock copolypeptide amphiphiles. Nature 2002, 417, (6887), 424-428.
Oeding, et al., Immunochemical Studies on Antigen Preparations from *Staphylococcus aureus*. 2. Precipitating and Erythrocyte-Sensitizing Properties of Protein a (Antigen a) and Related Substances. Acta Pathol. Microbiol. Scand. 1964, 62, 117-127.
Office Action for CN Application No. 201880068434.1, mailed Nov. 4, 2022, 10 pages.
Office Action for JP 2020-509080, mailed Apr. 4, 2023, 3 pages. With English translation.
Office Action for JP Application No. 2020-509080, mailed Jul. 12, 2022, 10 pages.
Olszewski et al.,Folding simulations and computer redesign of protein A three-helix bundle motifs. Proteins 1996, 25.
Palmer, et al., Molecular self-assembly into one-dimensional nanostructures. Accounts of chemical research 2008, 41, (12), 1674.
Paramonov, et al., Self-assembly of peptide-amphiphile nanofibers: the roles of hydrogen bonding and amphiphilic packing. Journal of the American Chemical Society 2006, 128, (22), 7291-7298.
Pille, J., et al., "General Strategy for Ordered Noncovalent Protein Assembly on Well-Defined Nanoscaffolds" Biomacromolecules 2013, 14, 4351-4359; dx.doi.org/10.1021/bm401291u.
Presta, Antibody engineering., Curr. Op. Struct. Biol. 2:593-596 (1992).
Richmond, et al., Packing of alpha-helices: Geometrical constraints and contact areas. J. Mol. Biol. 1978, 119, (4), 537-555.
Riechmann et al., Reshaping human antibodies for therapy Nature 332:323-329 (1988).
Rudra, et al., Modulating adaptive immune responses to peptide self-assemblies. Acs Nano 2012, 6, (2), 1557.
Sheth et al., Affinity precipitation of a monoclonal antibody from an industrial harvest feedstock using an ELP-Z stimuli responsive biopolymer. Biotechnol Bioeng 2014, 111 (8), 1595-603.
Sheth et al., Development of an ELP-Z based mAb affinity precipitation process using scaled-down filtration techniques. J Biotechnol 2014, 192 Pt A, 11-9.
Shimada et al., Wormlike micelle formation in peptide-lipid conjugates driven by secondary structure transformation of the headgroups. The journal of physical chemistry. B 2009, 113 (42), 13711-4.
Shukla et al., Downstream processing of monoclonal antibodies—application of platform approaches. J Chromatogr B Analyt Technol Biomed Life Sci 2007, 848 (1), 28-39.

(56) References Cited

OTHER PUBLICATIONS

Smith, et al., Fmoc-Diphenylalanine Self Assembles to a Hydrogel via a Novel Architecture Based on Π-π Interlocked β-Sheets. Advanced Materials 2008, 20, (1), 37-41.
Sorokina, I.A., et al., "Guidance manual, large laboratory practical course 2" Biochemistry of Proteins and Peptides, Rostov-on-Don, 2010, p. 96.
Starovasnik et al., Structural mimicry of a native protein by a minimized binding domain. Proceedings of the National Academy of Sciences 1997, 94 (19), 10080-10085.
Strable, E., et al., "Unnatural Amino Acid Incorporation into Virus-Like Particles" Bioconjug Chem. Apr. 2008 ; 19(4): 866-875. doi:10.1021/bc700390r.
Stuart, et al., The use of Nile Red to monitor the aggregation behavior in ternary surfactant-water-organic solvent systems. Journal of physical organic chemistry 2005, 18, (9), 929-934.
Takahashi, et al., Optimization of hydrophobic domains in peptides that undergo transformation from α- helix to β-fibril. Bioorganic & medicinal chemistry 1999, 7, (1), 177-185.
Taylor et al. A transgenic mouse that expresses a diversity of human sequence heavy and light chain immunoglobulins (1992) Nucleic Acids Research 20:6287-6295.
Taylor et al., Human immunoglobulin transgenes undergo rearrangement, somatic mutation and class switching in mice that lack endogenous IgM. (1994) International Immunology 6: 579-591.
Trent et a., Structural properties of soluble peptide amphiphile micelles. Soft Matter 2011, 7 (20), 9572-9582.
Trent, et al., Peptide amphiphile micelles self-adjuvant group A streptococcal vaccination. AAPS J 2015, 17, (2), 380-8.
Tuaillon et al. Human immunoglobulin heavy-chain minilocus recombination in transgenic mice: gene-segment use in mu and gamma transcripts.(1993) Proc. Natl. Acad. Sci. USA 90:3720-3724.
Tuaillon et al., Biased utilization of DHQ52 and JH4 gene segments in a human Ig transgenic minilocus is independent of antigenic selection. (1994) J. Immunol. 152:2912-2920.
Ulijn, et al., Designing peptide based nanomaterials. Chem Soc Rev 2008, 37, (4), 664-75.
Vaneldijk, M. , et al., "Thermodynamic investigation of Z33-antibody interaction leads to selective purification of human antibodies" Journal of Biotechnology 179 (2014) 32-41.
Vauthey, et al., Molecular self-assembly of surfactant-like peptides to form nanotubes and nanovesicles. Proceedings of the National Academy of Sciences 2002, 99, (8), 5355-5360.
Webber et al., Reprint of: Development of bioactive peptide amphiphiles for therapeutic cell delivery. Acta biomaterialia 2015, 23, S42-S51.
Webber, et al., Development of bioactive peptide amphiphiles for therapeutic cell delivery. Acta Biomater 2010, 6, (1), 3-11.
Wiseman et al., Rapid measurement of binding constants and heats of binding using a new titration calorimeter. Analytical biochemistry 1989, 179 (1), 131-137.
Xu, et al., Hydrophobic-region-induced transitions in self-assembled peptide nanostructures. Langmuir 2008, 25, (7), 4115-4123.
Zhao, et al., Molecular hydrogels of therapeutic agents. Chem Soc Rev 2009, 38, (4), 883-91.
Missirlis, D. et al. Mechanisms of peptide amphiphile internalization by SJSA-1 cells in vitro. Biochemistry. Apr. 21, 2009;48(15):3304-14.
Office Action for KR 10-2020-7007663, mailed Feb. 26, 2024, 9 pages. With English Translation.

\* cited by examiner

FIGURES 3A-3D
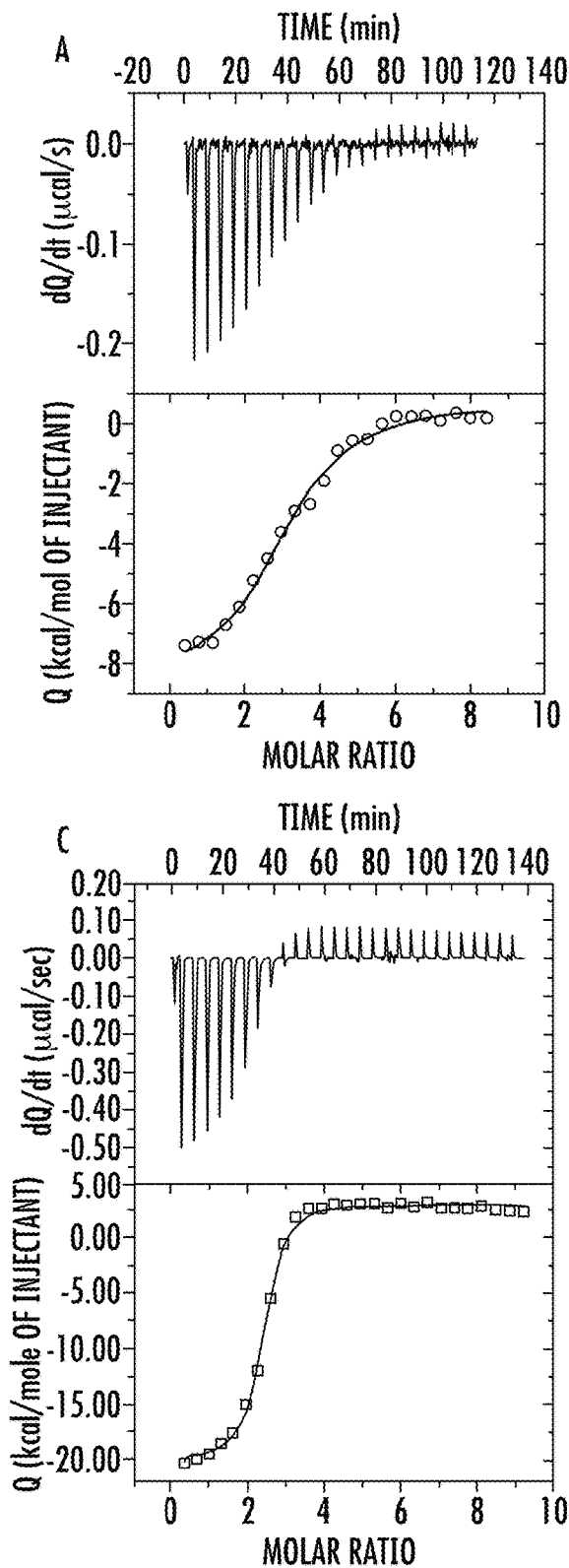
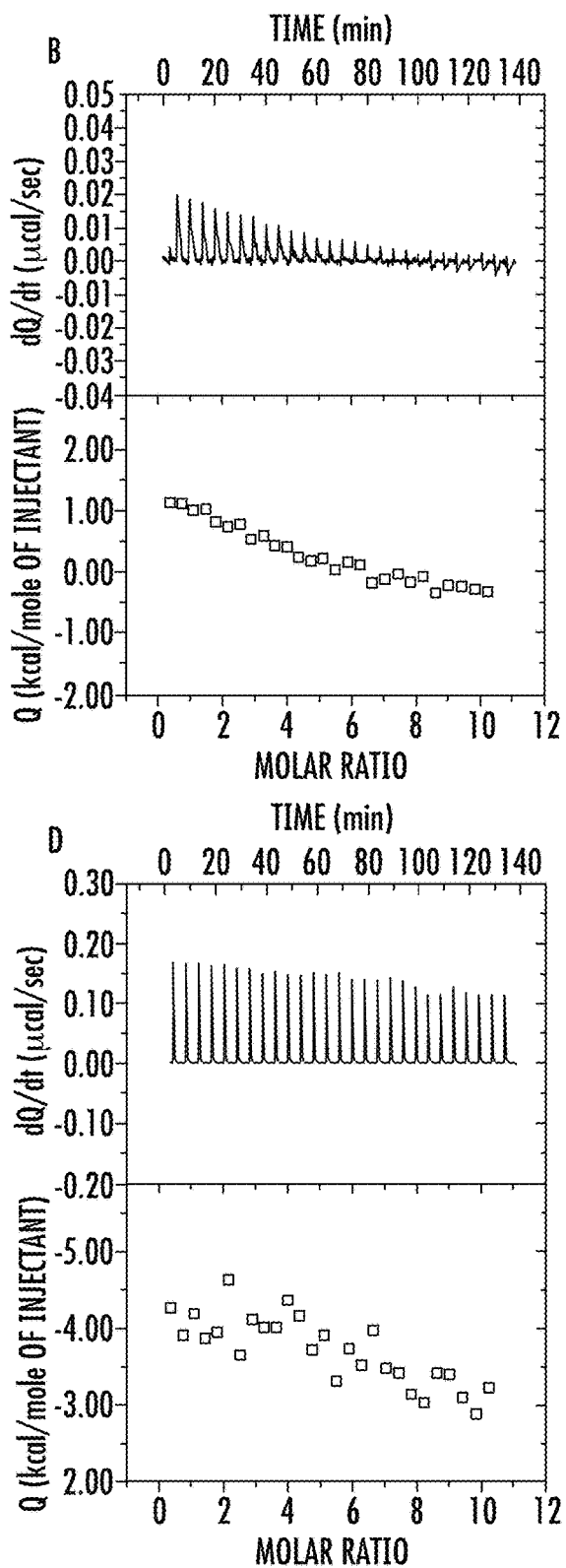

FIGURE 13    FNMQQQRRFYEALHDK-C8 (HELIX1-C8)(SEQ ID NO: 3)

FNMQQQRRFYEALHDK-C12 (HELIX1-C12) (SEQ ID NO: 3)

FNMQQQRRFYEALHDK-C16 (HELIX1-C16) (SEQ ID NO: 3)

FNMQQQRRFYEALHDKK-2C8 (HELIX1-2C8) (SEQ ID NO: 4)

SUPRAMOLECULAR FILAMENTOUS ASSEMBLIES FOR PROTEIN PURIFICATION

CROSS-REFERENCE TO RELATED APPLICATIONS

This application is a divisional of U.S. patent application Ser. No. 16/639,763, filed Feb. 18, 2020, now U.S. Pat. No. 11,745,165, issued Sep. 5, 2023, which is a 35 U.S.C. § 371 U.S. national entry of International Application PCT/US2018/046924, having an international filing date of Aug. 17, 2018, which claims the benefit of U.S. Provisional Application No. 62/547,256, filed Aug. 18, 2017, the content of each of the aforementioned applications is herein incorporated by reference in their entirety.

INCORPORATION-BY-REFERENCE OF MATERIAL SUBMITTED ELECTRONICALLY

The text of the computer readable sequence listing filed herewith, titled "JHU-39019-403_SQL", created Aug. 31, 2023, having a file size of 13,539 bytes, is hereby incorporated by reference in its entirety.

BACKGROUND OF THE INVENTION

Amphiphilic peptides or peptide conjugates that can self-assemble into one-dimensional (1D) nanostructures have been extensively investigated over the past two decades due to their important biomedical applications. In order to render the resulting self-assembled nanostructures with the ability to interface with biology, a variety of bioactive peptides have been incorporated into the molecular design. The challenge, however, remains to accurately control over the secondary structures of the bioactive peptide displayed on the supramolecular surfaces that are necessary for their proper funcations. In general, the eventual self-assembled morphologies are determined by several interplaying factors, which may include hydrophobic interactions, hydrogen bonding, electrostatic interactions, and π-π stacking. For peptide-based 1D nanostructures, β-sheet motifs are often used to provide intermolecular hydrogen bonding for anisotropic growth of the resultant assemblies. α-helical peptides, another essential constituents of proteins and also key mediators of many important biomolecular interactions, have also been employed, albeit less frequently, to create supramolecular nanostructures. For example, Tirrell and co-workers have designed cylindrical micelles and protein analogous micelles with significant α-helicity. Moreover, by tuning solvent property, hydrophobic tail, or thermal history, transitions in self-assembling peptide nanostructures among structures as diverse as random coil, α-helix, and β-sheet, have been occasionally reported. Despite these important progress, concerns still remain with its intrinsic thermodynamic instability and structural uncertainty of α-helical peptides within their supramolecular assemblies.

It has been shown that α-helical secondary structures can be stabilized by conjugation of alkyl chains. However, transitions from α-helix to β-sheet in one peptide by tuning the number of alkyl chains were rarely seen.

This direct placement of a bioactive peptide on either C- or N-terminus of a self-assembling peptide motif has become a popular strategy to create bioactive materials for a specific biomedical application. In an effort to modulate immunogenicity of peptide assemblies, Collier and coworkers covalently linked the self-assembling peptide Q11 to an antigen OVA peptide and found that the resultant supramolecular OVA-Q11 nanofibers possess enhanced immunogenicity. Thus far, there have been numerous studies in the literature that have well demonstrated that biologically active peptides can be successfully incorporated into supramolecular peptide nanostructures while maintaining their bioactivities. However, in the cases where the epitope has to retain an α-helical conformation to be bioactive, there seems to be a spacing incompatibility issue between the use of β-sheet-forming sequence and the presentation of α-helical motif.

High affinity antibody-binding particles and materials are receiving rapidly growing interest in pharmaceutical industry, as driven by the increasing demand of monoclonal antibodies for biological therapeutics. Protein A, a well-known antibody-binding ligand, has the capacity of specific binding to the Fc-portion of IgG from most mammalian species, including human However, the large size of protein A limits its industrial application, and as such a number of synthetic and minimized domains of protein A have been designed and studied. The Z-domain of protein A is the first and most famous synthetic domain with 59 amino acid residues and a $K_d$ of ~10 nM when binding to IgG1. To further minimize the Z-domain of protein A, a two-helix derivative Z33 was designed without significantly changing the binding affinity ($K_d$=43 nM). While a high affinity ligand has been identified, the way to present ligands on a desired substrate is equally essential for the antibody purification process. In pharmaceutical industry, antibody purification mainly relies on affinity chromatography based on immobilization of antibody binding ligands (e.g., protein A) with high selectivity but suffering from the high chromatography media cost and limited capture productivity. It is only until recently that affinity precipitation became an attractive alternative to traditional chromatographic methods by offering effective purification and potentially debottlenecking batch throughput using a relatively simple process.

A typical example of affinity precipitation is the use of elastin-like-protein (ELP) fused Z-domain to precipitate IgG through the temperature and salt triggered solubility transition of ELP. However, the high mass of ELP expressed by bacteria, limited binding sites on each ELP fused ligand, and potential denaturation of antibody at elevated temperature promote the interest of finding the new substrates to present antibody-binding ligands.

Inspired by the elegant molecular design of self-assembling peptide amphiphiles, the present inventors previously described a way of incorporating the protein A mimicking peptide Z33 into self-assembling immuno-amphiphiles (IAs) and explored its binding ability to the target antibody in the self-assembled state. The binding affinity between the self-assembled immunofibers (IFs) and therapeutic IgG were investigated using isothermal titration calorimetry (ITC), suggesting that the Z33 containing IFs maintains its high IgG binding affinity.

The present inventors investigated whether the peptide can be fragmented and conjugated to alkyl chains to change the conformational structure of the fragmented peptides and still retain self-assembling immuno-amphiphilic properties that can be combined for effective protein purification.

SUMMARY OF THE INVENTION

Many one-dimensional (1D) nanostructures are constructed by self-assembly of peptides or peptide conjugates containing a short β-sheet sequence as the core building motif essential for the intermolecular hydrogen bonding that promotes directional, anisotropic growth of the resultant assemblies. While this molecular design strategy has led to the successful production of a plethora of bioactive filamentous β-sheet assemblies for interfacing with cells, concerns associated with potential toxicity reminiscent of amyloid fibrils have promoted other supramolecular crafting strategies with α-helical peptides.

The present inventors previously showed that the direct conjugation of the protein A mimicking peptide Z33, having the amino acid sequence FNMQQQRRFYEALHDPNLNEEQRNAKIKSIRDD (SEQ ID NO: 1), a motif containing two α-helices, to linear hydrocarbons created self-assembling immuno-amphiphiles. The results show that the resulting amphiphilic peptides can, despite lacking the essential β-sheet segment, effectively associate under physiological conditions, into supramolecular immunofibers (IFs) while preserving their native α-helical conformation. Isothermal titration calorimetry measurements confirmed that these self-assembling immunofibers can bind to the immunoglobulin G (IgG) antibody with high specificity at pH 7.4, but no detectable binding occurred in elution buffer, pH 2.8.

The present invention provides a molecular strategy of switching the secondary structure of α-helical peptides between α-helix and β-sheet by single-chain or double-chain alkylation. Two peptide sequence fragments, isolated from the α-helical peptide Z33, which was derived from protein A, were designed to serve as the hydrophilic segment in the immuno-amphiphiles (IAs). It is anticipated that these self-assembling immunofibers, when combined in solution, can bind to the immunoglobulin G (IgG) antibody with high specificity at pH 7.4.

Thus, in some embodiments, the supramolecular engineering of protein binding peptides into self-assembling immunofibers useful for effective protein purification.

In accordance with an embodiment, the present invention provides an immuno-amphiphile comprising an antibody binding peptide conjugated to a linear hydrocarbon chain.

In accordance with an embodiment, the present invention provides self-assembling immunofibers comprising immuno-amphiphiles comprising an antibody binding peptide conjugated to a linear hydrocarbon chain and wherein the immuno-amphiphile has an α-helical conformation when in an aqueous solution at physiological pH.

In accordance with an embodiment, the present invention provides self-assembling immunofibers comprising immuno-amphiphiles comprising an antibody binding peptide conjugated to a linear hydrocarbon chain, wherein the antibody binding peptide has a hydrophilic amino acid sequence of the Z33 peptide of Protein A of *Staphylococcus aureus*, or a functional portion or fragment or derivative thereof.

In accordance with an embodiment, the present invention provides self-assembling immunofibers comprising immuno-amphiphiles comprising a fragment of an antibody binding peptide conjugated to a linear hydrocarbon chain.

In accordance with an embodiment, the present invention provides self-assembling immunofibers comprising immuno-amphiphiles comprising a fragment of an antibody binding peptide conjugated to a linear hydrocarbon chain and wherein the immuno-amphiphile has an α-helical conformation when in an aqueous solution at physiological pH.

In accordance with an embodiment, the present invention provides self-assembling immunofibers comprising immuno-amphiphiles comprising a fragment of an antibody binding peptide conjugated to a linear hydrocarbon chain and wherein the immuno-amphiphile has an β-sheet conformation when in an aqueous solution at physiological pH.

In accordance with an embodiment, the present invention provides self-assembling immunofibers comprising immuno-amphiphiles comprising a fragment of an antibody binding peptide conjugated to a linear hydrocarbon chain, wherein the antibody binding peptide has a portion of the hydrophilic amino acid sequence of the Z33 peptide of Protein A of *Staphylococcus aureus*.

In accordance with another embodiment, the present invention provides an immunofiber composition comprising one or more immuno-amphiphiles comprising an antibody binding peptide conjugated to a linear hydrocarbon chain, wherein the antibody binding peptide has a hydrophilic amino acid sequence of the Z33 peptide of Protein A of *Staphylococcus aureus*, or a functional portions or fragments or derivatives thereof.

In accordance with an embodiment, the present invention provides a method for purification of proteins comprising contacting a solution at a first pH level containing one or more proteins of interest, with an immunofiber composition comprising one or more immuno-amphiphiles comprising an antibody binding peptide conjugated to a linear hydrocarbon chain, wherein the antibody binding peptide has a hydrophilic amino acid sequence of the Z33 peptide of Protein A of *Staphylococcus aureus*, or functional portions or fragments or derivatives thereof; allowing the one or more proteins of interest to bind the antibody binding peptide or functional portions or fragments or derivatives thereof; changing the pH level of the solution to a pH which changes the charge properties and conformation of the antibody binding peptide and the one or more proteins of interest; and extracting the released one or more proteins of interest from the solution.

In accordance with a further embodiment, the present invention provides an immunofiber composition comprising an immunofiber binding molecule comprising an antibody binding peptide conjugated to a linear hydrocarbon chain at its N-terminus, and conjugated to a first spacer peptide conjugated to an antibody binding peptide having a hydrophilic amino acid sequence of the Z33 peptide of Protein A of *Staphylococcus aureus,* or functional portions or fragments or derivatives thereof at its C-terminus, and wherein the first spacer peptide comprises the generic sequence of XXYYZZ, wherein XX is two amino acids having a small hydrophobic side chain and can be the same or different amino acid, YY is two amino acids having a positively charged side chain and can be the same or different amino acid, and ZZ is two amino acids having a small neutral side chain and can be the same or different amino acid, and further comprising an immunofiber spacer molecule having a linear hydrocarbon chain at its N-terminus conjugated to a peptide sequence comprising the generic sequence of XXBB, wherein XX is two amino acids having a small hydrophobic side chain and can be the same or different amino acid, and wherein BB is two amino acids having a negatively charged side chain, and can be the same or different amino acid.

In accordance with another embodiment, the present invention provides a methods for making an immunofiber composition comprising one or more immuno-amphiphiles comprising an antibody binding peptide conjugated to a linear hydrocarbon chain, wherein the antibody binding peptide has a hydrophilic amino acid sequence of the Z33 peptide of Protein A of *Staphylococcus aureus*, or a functional portions or fragments or derivatives thereof.

BRIEF DESCRIPTION OF THE DRAWINGS

FIGS. 1A-1C. (1A) Schematic illustration of the Z33 peptide binding to Fc-portion of IgG. (1B) The sequences of C12-Z33 and 2C8-Z33. Alkyl groups and Z33 are indicated. The two α-helices in Z33 peptide are underlined. (1C) Schematic illustration of the self-assembly of R-Z33 IFs and the binding between IFs and IgG.

FIGS. 2A-2F. (2A) Schematic illustration of self-assembly of C12-Z33. (2B) Normalized CD Spectra of Z33 peptide and Z33-C12 at pH 7.4 and 2.8, respectively. TEM characterization of C12-Z33 at pH 7.4 (2C, D) and 2.8 (2E, F). The TEM samples were prepared at concentration of 100 μM in PBS (pH 7.4) and IgG elution buffer (pH 2.8) separately. The TEM samples were negatively stained with 2 wt % uranyl acetate.

FIGS. 3A-3D. ITC profiles for the titration of 100 μM C12-Z33 into a solution of 2 μM IgG1 at 15° C. in (3A) PBS buffer, pH 7.4, and (3B) IgG elution buffer, pH 2.8. ITC profiles for the titration of 100 μM (3C) Z33 and (3D) C12-SZ33 into 2 μM IgG1 in PBS at 15° C., pH 7.4.

FIGS. 4A-4E. TEM characterization of 2C8-Z33 in (4A) PBS at pH 7.4 with a diameter of 16.8±1.5 nm and (4B) IgG elution buffer at pH 2.8 with a diameter of 17.3±1.9 nm. The preparation of TEM sample was similar with that of C12-Z33. (4C) Normalized CD Spectra of 100 μM 2C8-Z33 in PBS at pH 7.4 showed α-helix secondary structures. ITC profiles for the titration of 100 μM 2C8-Z33 into a solution of 2 μM IgG1 in (4D) PBS buffer, pH 7.4 and (4E) IgG elution buffer, pH 2.8.

FIGS. 5A-5D. (5A) Schematic illustration of the precipitation of IFs-IgG complexes triggered by 0.6 M $Na_2SO_4$ solution. (5B) Photographs of 5 mM PBS solution of C12-Z33 (i) before and (ii) after addition of 0.6 M $Na_2SO_4$ and 20 μM PBS solutions of IgG1 with (iii) 5 mM C12-Z33, (iv) 0.6 M $Na_2SO_4$, and (v) 5 mM C12-Z33 and 0.6 M $Na_2SO_4$. Precipitation were observed in (ii) and (v). (5C) Absorbance spectra of C12-Z33 and IgG1+C12-Z33 complexes before and after addition of 0.6 M $Na_2SO_4$. The supernate of net IgG1 is derived from the supernate of IgG1+C12-Z33 subtracted by the supernate of C12-Z33. (5D) Absorbance spectra of 2 mM C12-SZ33 and IgG1+C12-SZ33 complexes before and after addition of 0.6 M $Na_2SO_4$.

Figures 6A, 6B:
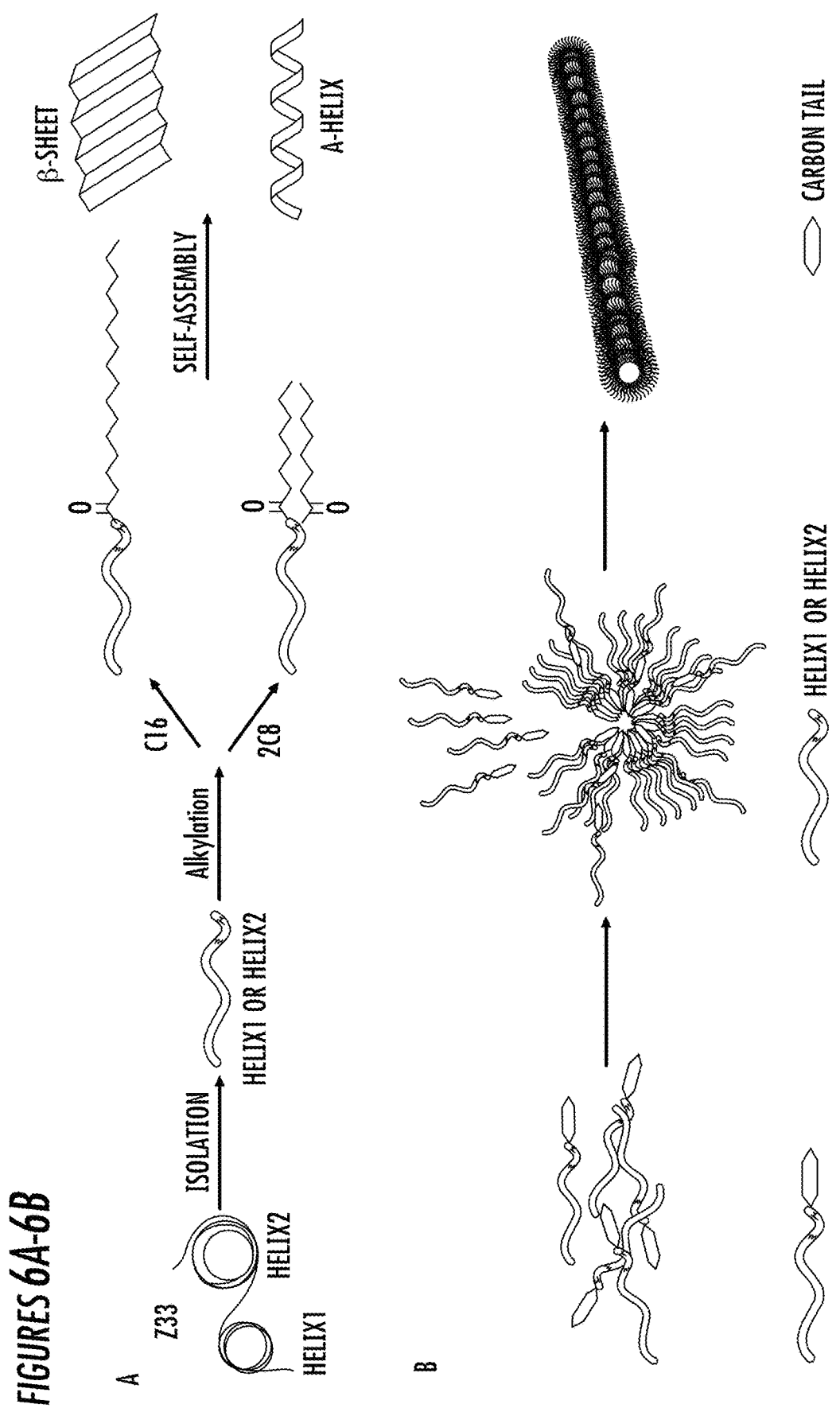

FIGS. 6A-6B. (6A) Schematic illustration of the design of the exemplary embodiments of Helix1- and Helix2-based peptide amphiphiles via direct alkylation with C16 and 2C8, respectively. (6B) Schematic illustration of the self-assembly of IA molecules into one dimensional nanostructures.

FIGS. 7A-7D. TEM images of different IAs. TEM images of (7A) Helix1-C16 and (7C) C16-Helix2 display nanofibers morphology with diameters of 9.5±1.2 nm and 12.4±1.7 nm, respectively. TEM images of (7B) Helix1-2C8 and (7D) 2C8-Helix2 display nanobelts morphology with diameters of 10-70 nm and 22.9±1.5 nm, respectively. All the samples were prepared in water at 1 mM, pH 7.4 and aged overnight before imaging. The TEM samples were negatively stained with 2 wt % uranyl acetate. Scale bars: 200 nm.

FIGS. 8A-8D. Emission spectra of the reporter dye Nile Red when incubated with (8A) Helix1-C16, (8B) C16-Helix2, (8C) Helix1-2C8, and (8D) 2C8-Helix2 for determining the critical micelle concentration (CMC) values. All spectra shown here are normalized by the emission maximum, and display a blue-shift when the conjugate concentrations surpass the CMC. The CMC range for each IA is boxed in the legend. Unit: μM.

Figures 9A, 9B:
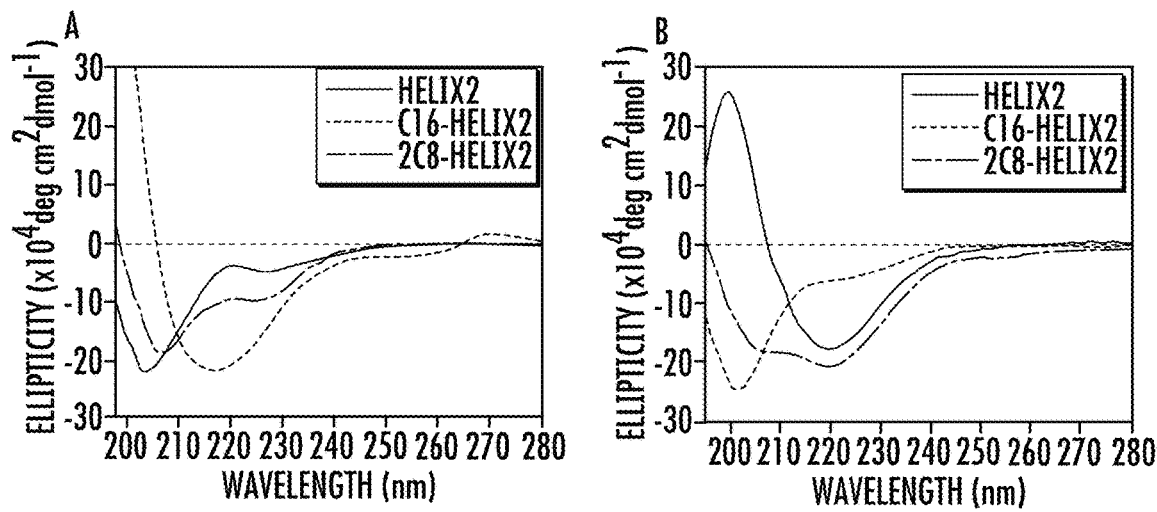

FIGS. 9A-9B. Normalized CD Spectra of 100 μM (9A) Helix1, Helix1-C16, Helix1-2C8, and (9B) Helix2, C16-Helix2, 2C8-Helix2 in water at pH 7.4.

Figures 10A, 10B:
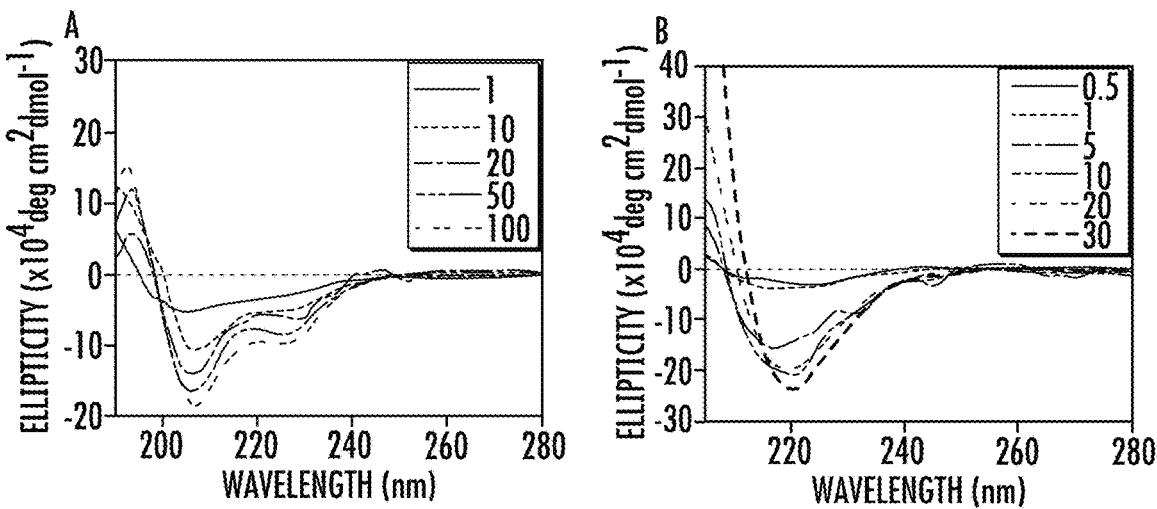
Figures 11A, 11B, 11C, 11D, 11E, 11F:
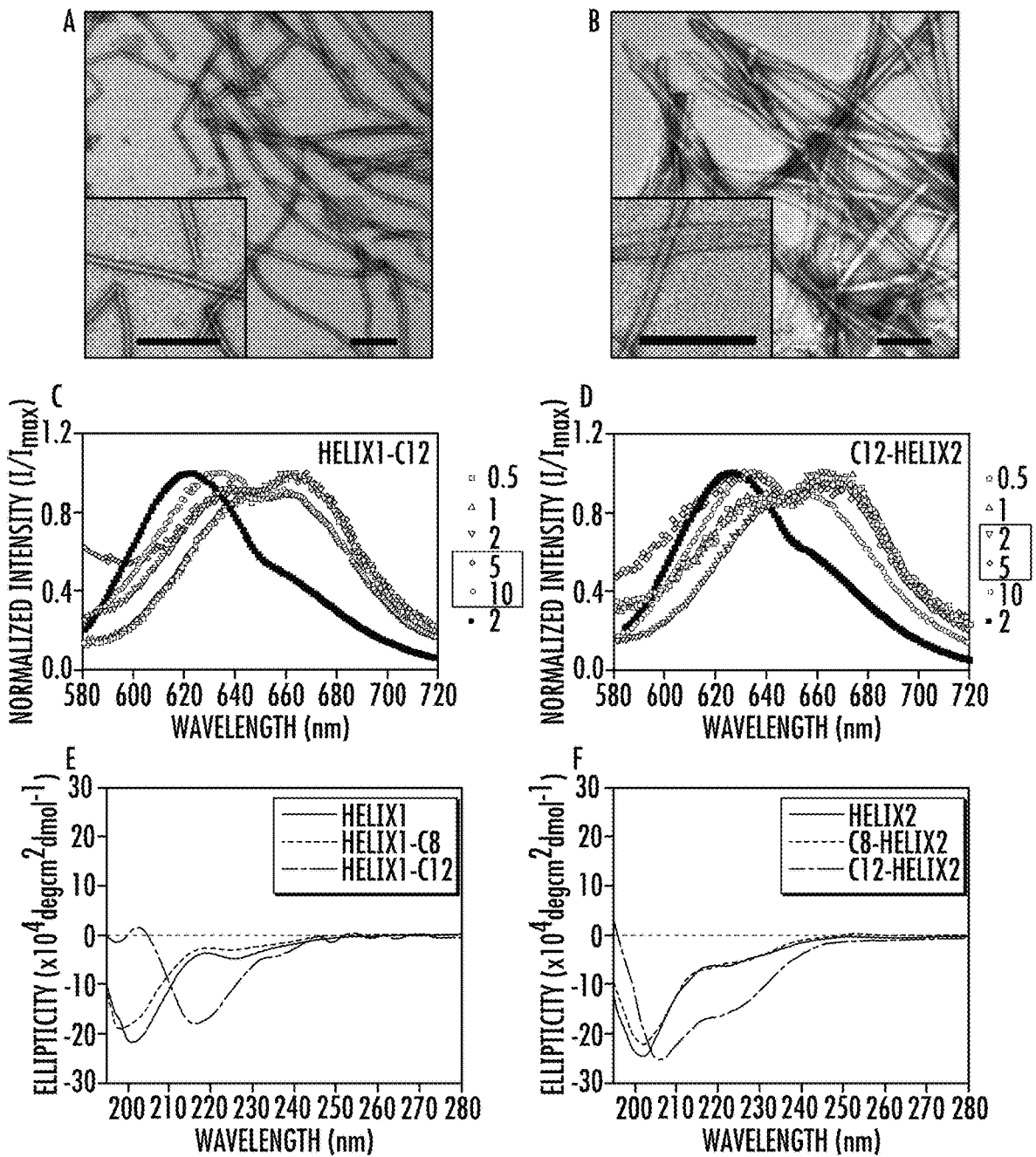

FIGS. 10A-10B. Normalized CD Spectra of (10A) Helix1-2C8 and (10B) Helix1-C16 at different concentrations in water at pH 7.4. The unit of the concentration is μM.

FIGS. 11A-11F. TEM images of different IAs. TEM images of (11A) Helix1-C12 and (11B) C12-Helix2 display nanofibers morphology with diameters of 12.9±0.9 nm, and 13.9±1.5 nm, respectively. Scale bars: 200 nm. Emission spectra of the reporter dye Nile Red when incubated with (11C) Helix1-C12 and (11D) C12-Helix2 for determining the critical micelle concentration (CMC) values. The unit of the concentration is μM. Normalized CD Spectra of 100 μM (11E) Helix1, Helix1-C8, Helix1-C12 and (11F) Helix2, C8-Helix2, C16-Helix2 in water at pH 7.4.

Figure 12:
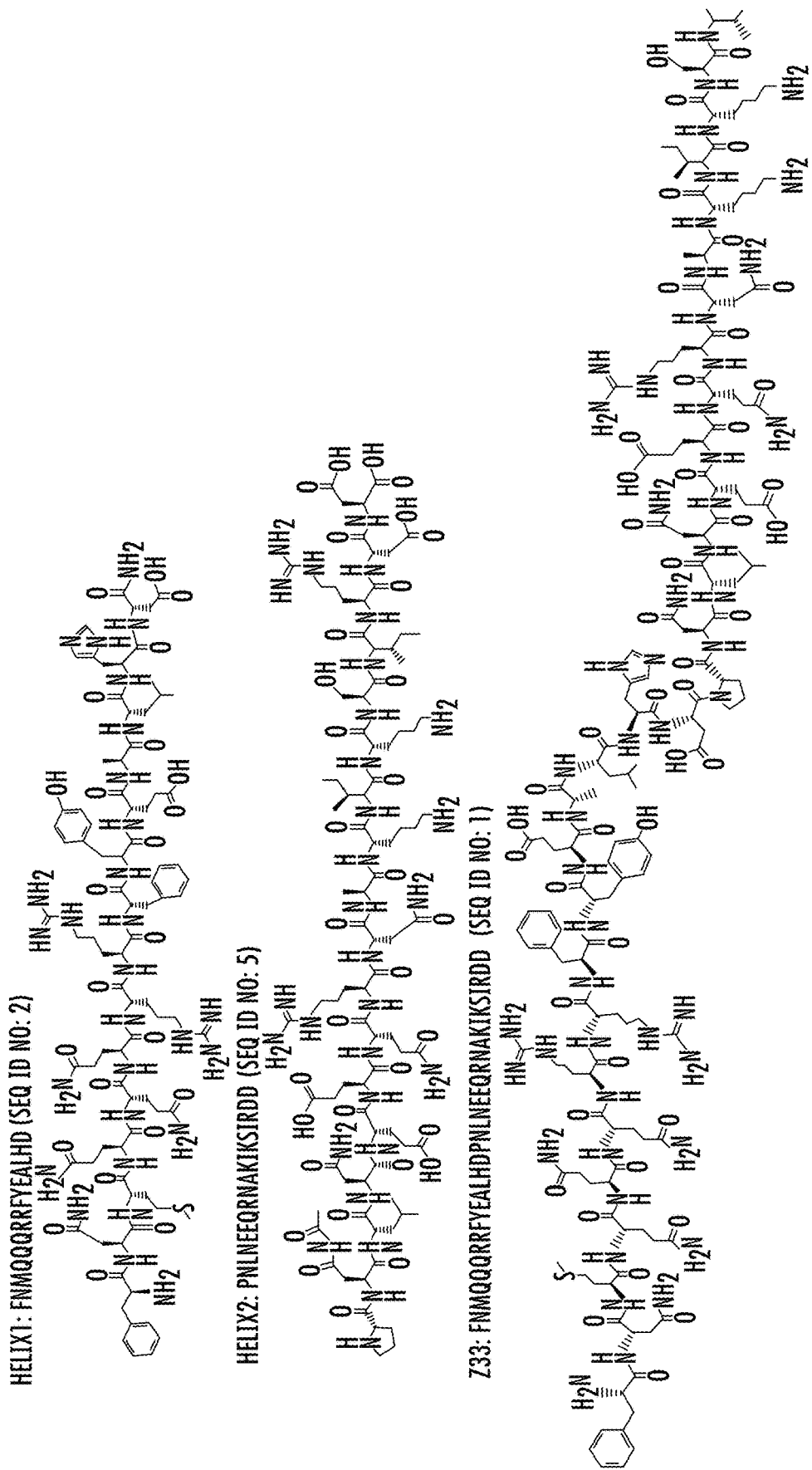

FIG. 12. The chemical structures of some exemplary embodiments of the fragment of antibody binding peptide sequences of Helix1, Helix2, and Z33.

Figure 13:
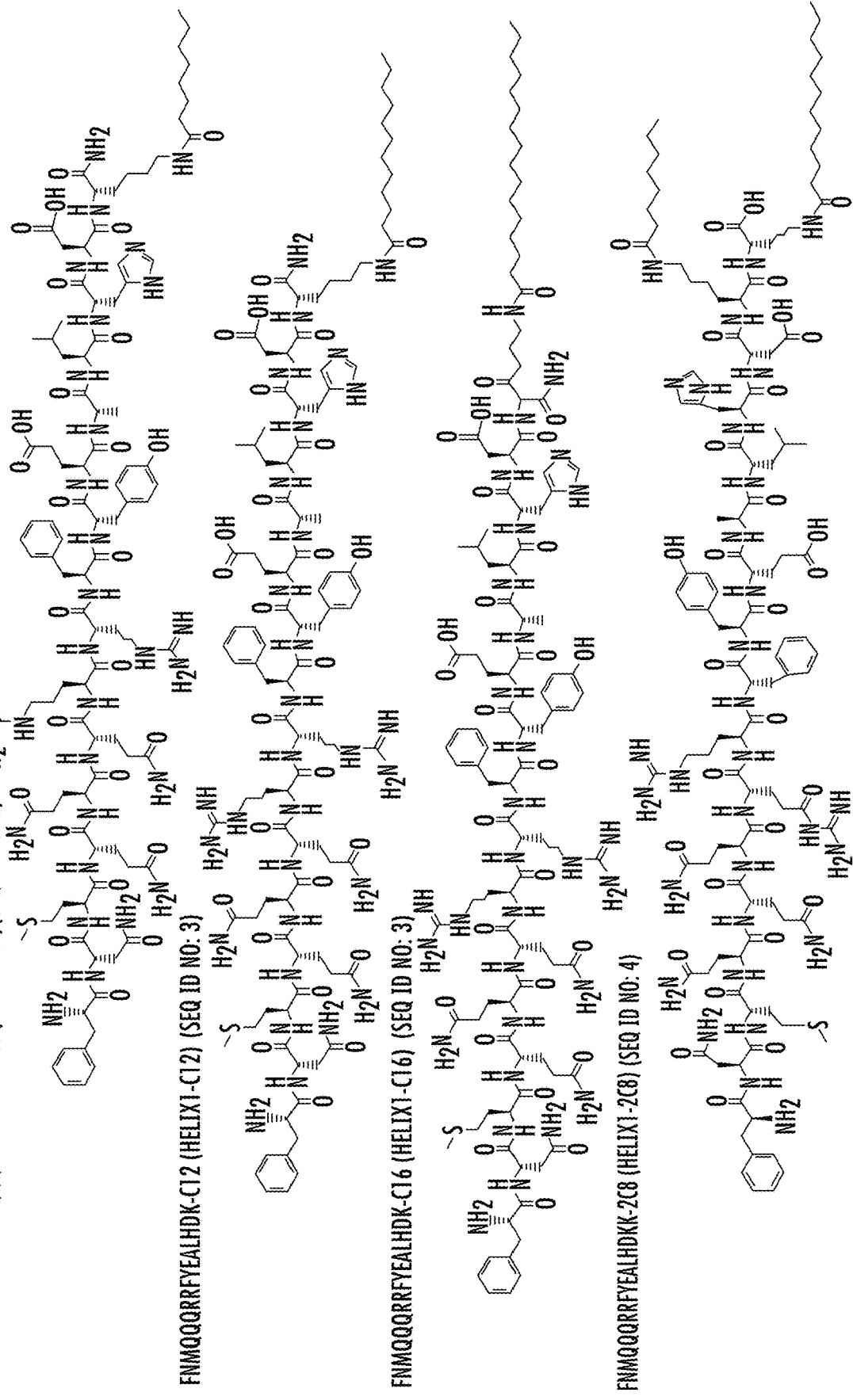

FIG. 13. The chemical structures of the some exemplary fragments of antibody binding peptide sequences of Helix1-C8, Helix1-C12, Helix1-C16 and Helix1-2C8.

Figure 14:
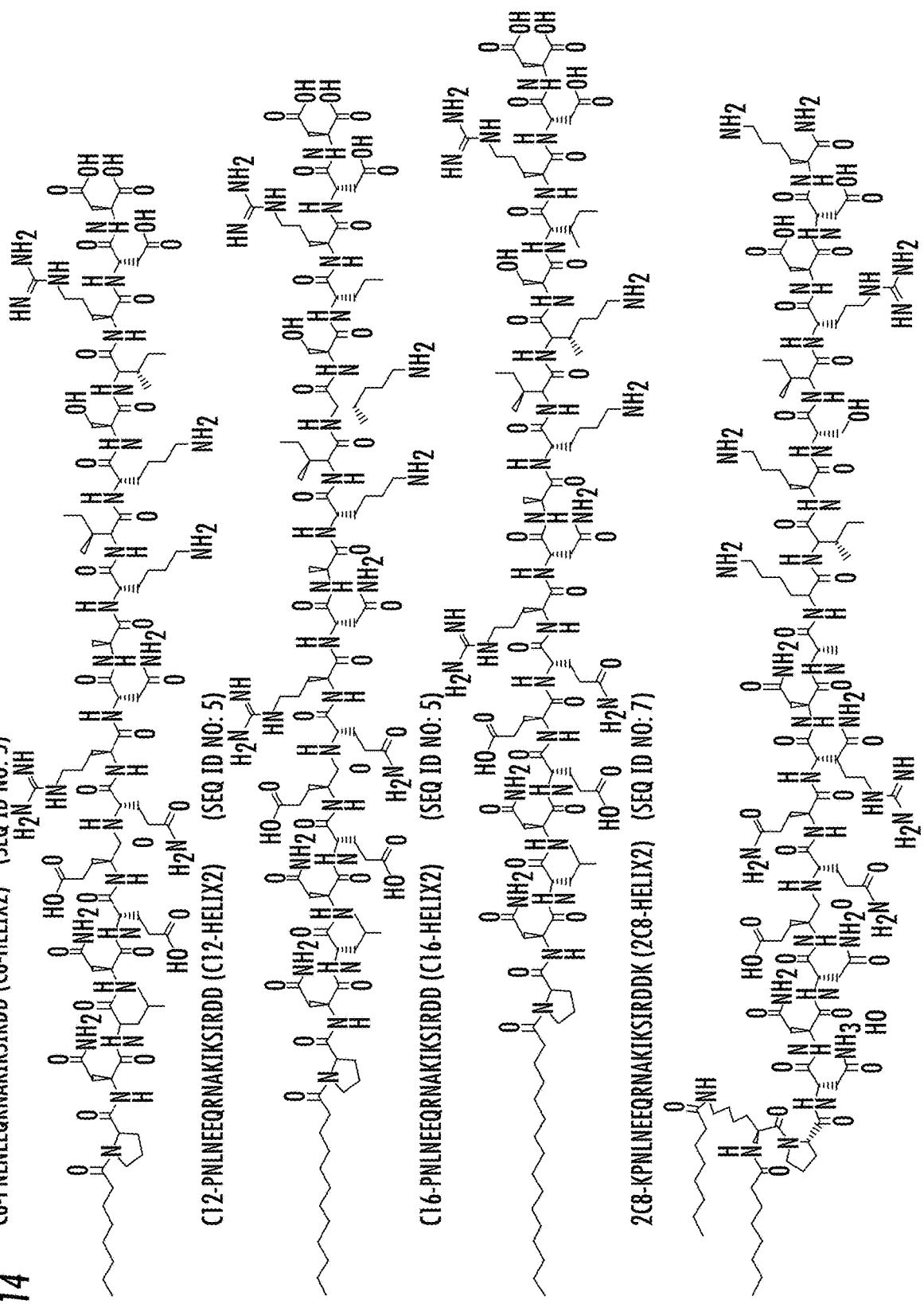

FIG. 14. The chemical structures of the fragment of some exemplary antibody binding peptide sequences of C8-Helix2, C12-Helix2, C16-Helix2, and 2C8-Helix2.

Figure 15A:
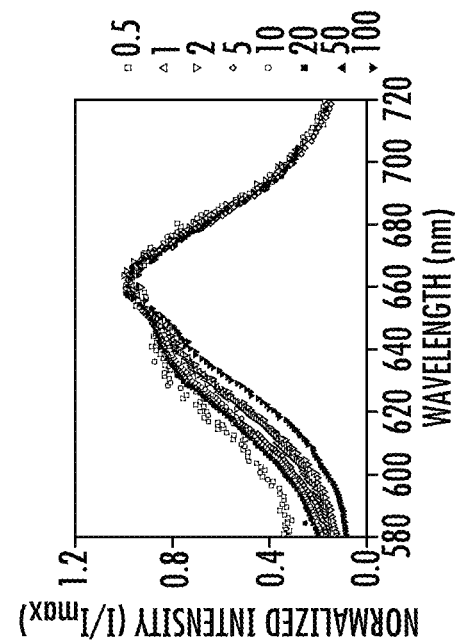
Figure 15B:
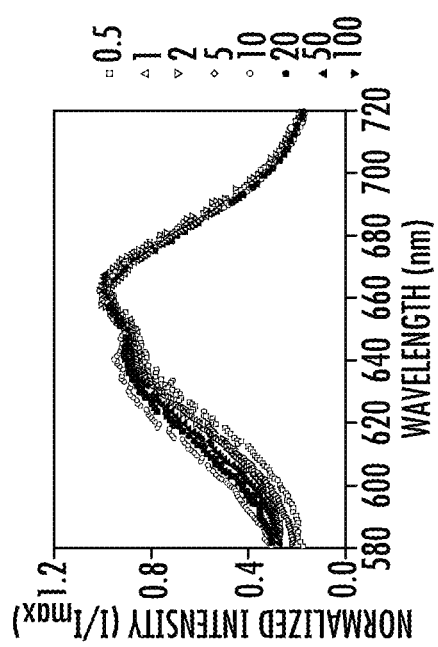

FIGS. 15A-15B. Emission spectra of the reporter dye Nile Red when incubated with (15A) Helix1-C8, (15B) C8-Helix2 for determining the critical micelle concentration (CMC) values. All spectra shown here are normalized by the emission maximum. The unit of the concentration is μM. There was no detectable peak shift observed even the conjugate concentrations reached 100 μM.

Figure 16:
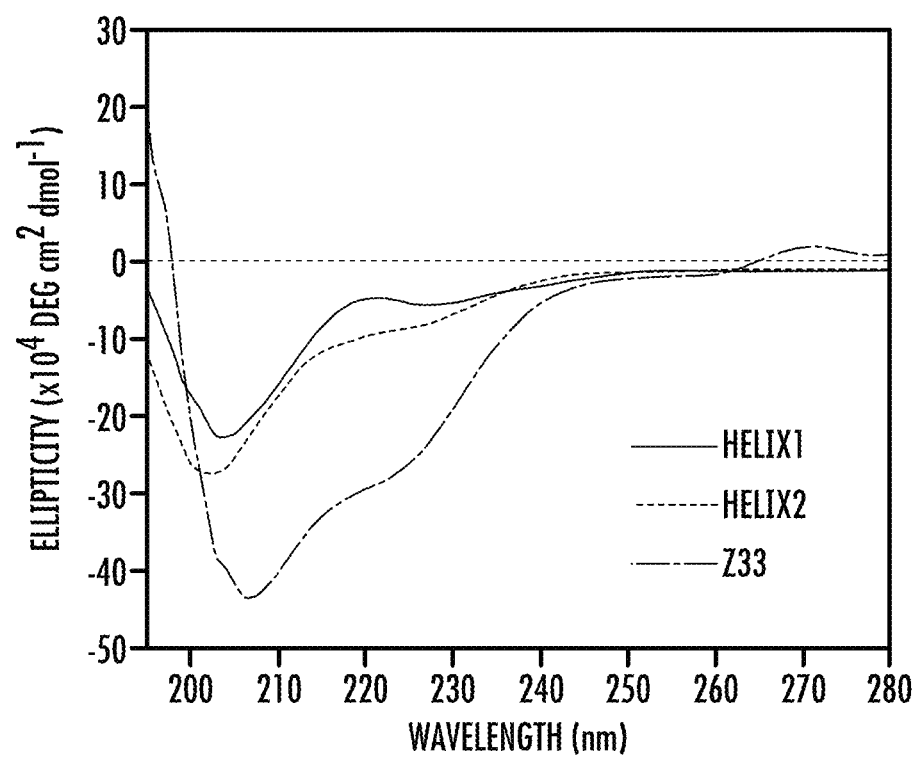

FIG. 16. Normalized CD Spectra of Helix1, Helix2, and Z33 at 100 μM in water at pH 7.4.

Figure 17A:
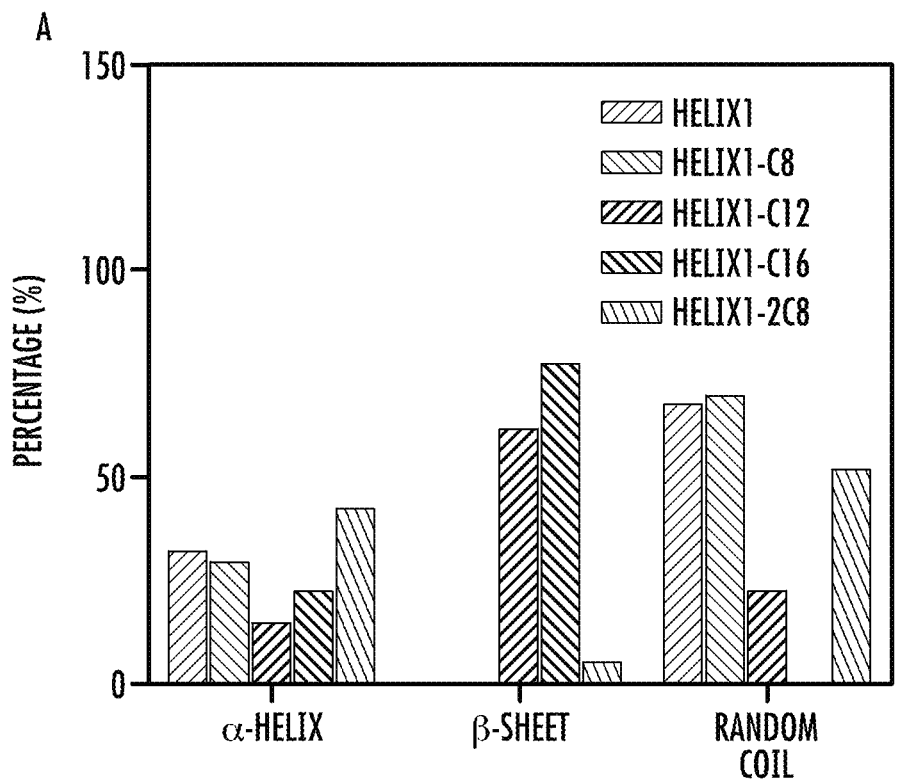
Figure 17B:
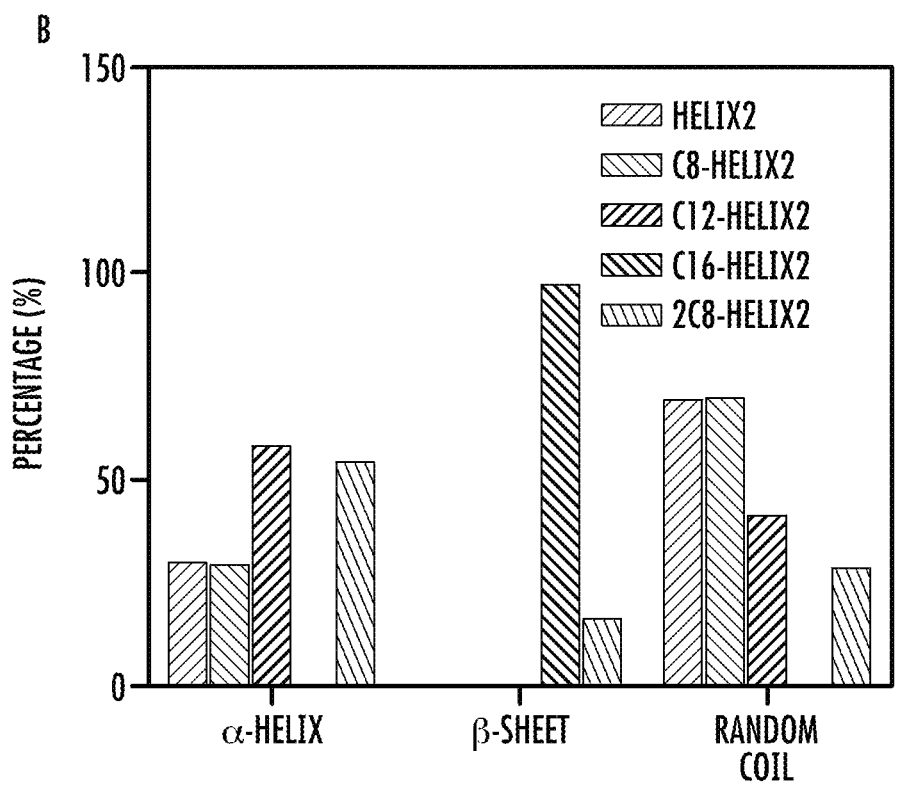

FIGS. 17A and 17B. Analysis of CD spectra for Helix1 and Helix2 based IAs. The content of three main secondary structures in (FIG. 17A) Helix1-based and (FIG. 17B) Helix2-based molecules. The CD data were fit from 200 to 240 nm using a linear combination of polylysine basis spectra to determine approximate α-helix, β-sheet, and random coil peptide secondary structure.

Figure 18:
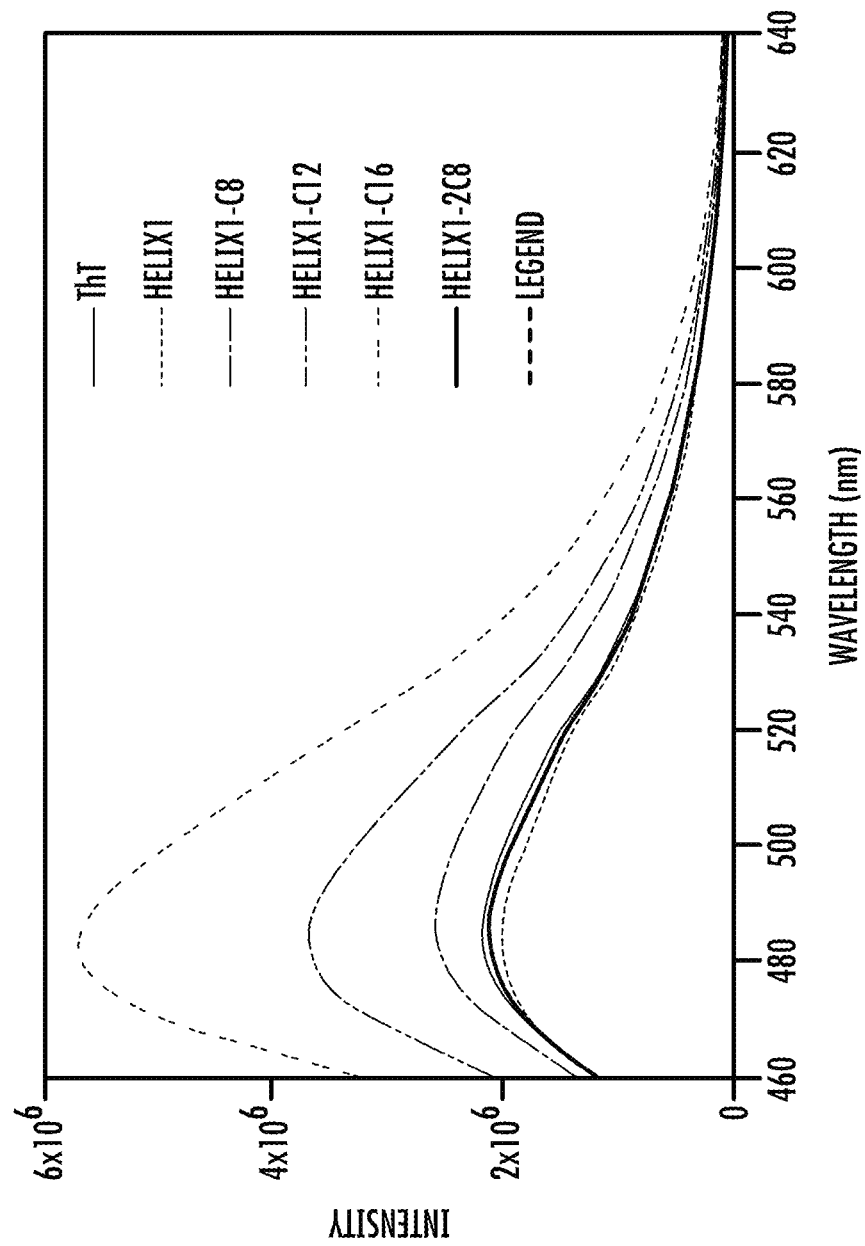

FIG. 18. Fluorescence of ThT dye with Helix1 and Helix1-based peptide amphiphiles at 100 μM in deionized water.

Figures 19A, 19B:
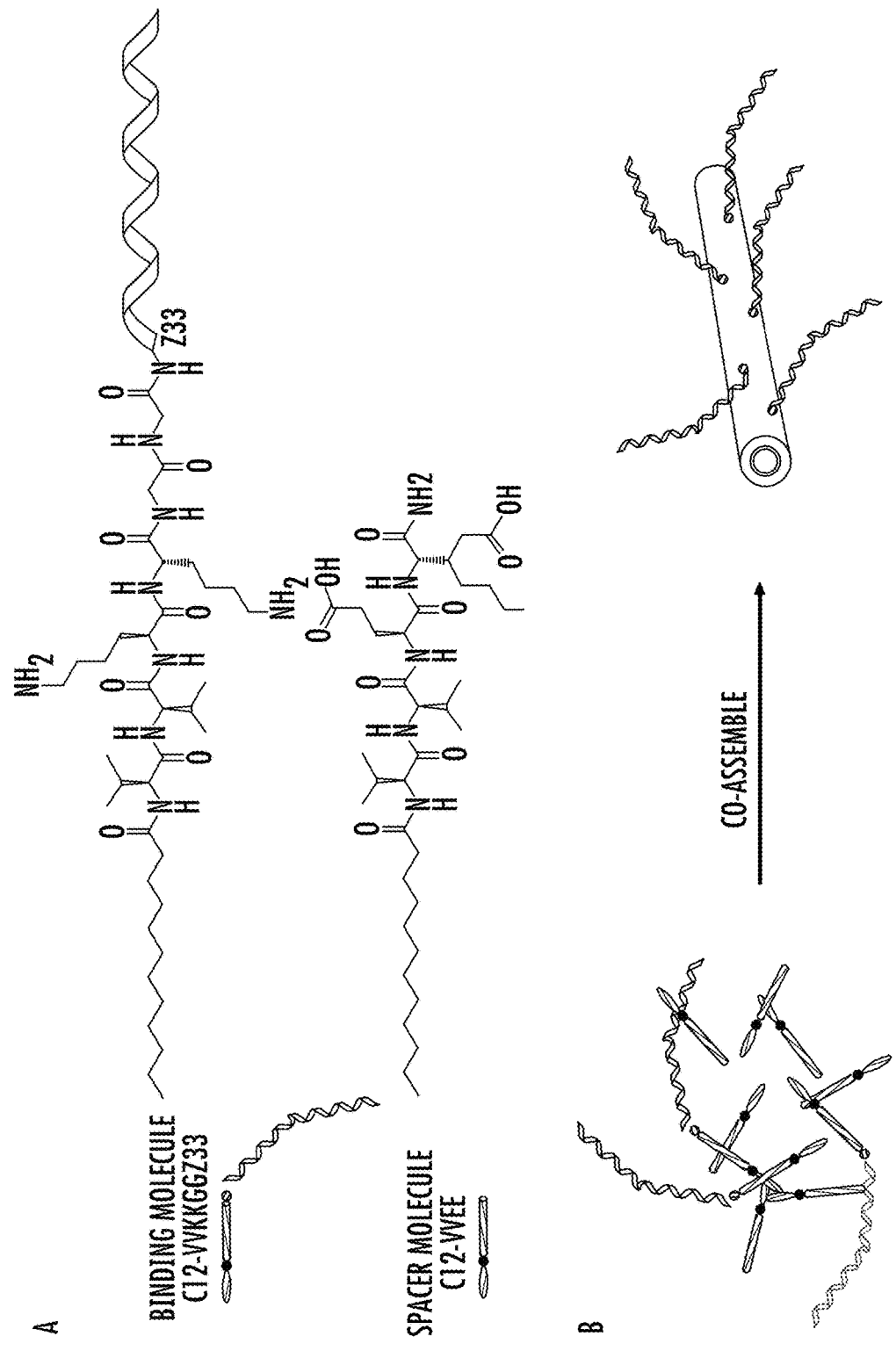

FIG. 19A-B. (19A) Chemical structures of alternative embodiment binding molecule C12-VVKKGG (SEQ ID NO: 9) -Z33 and spacer molecule C12-VVEE (SEQ ID NO: 10). Alkyl tail were conjugated to the N-terminus of the peptide sequence. Two valines (VV) promotes the formation of one-dimensional structures. Two glutamic acids (EE) were designed as the hydrophilic segment in the spacer molecule and two lysine (KK) were designed accordingly for electrostatic interactions between KK and EE and thus inducing the alternating packing of binding and spacer molecules. Two glycine (GG) were designed for further separating Z33 from the alkyl chains. (19B) Schematic illustration of co-assembly of C12-VVKKGG (SEQ ID NO: 9) -Z33 and C12-VVEE (SEQ ID NO: 10). The density of the binding molecule on the surface of the co-assembled immunofibers can be easily controlled by tuning the molar ratio of binding and spacer molecules.

Figures 20A, 20B, 20C:
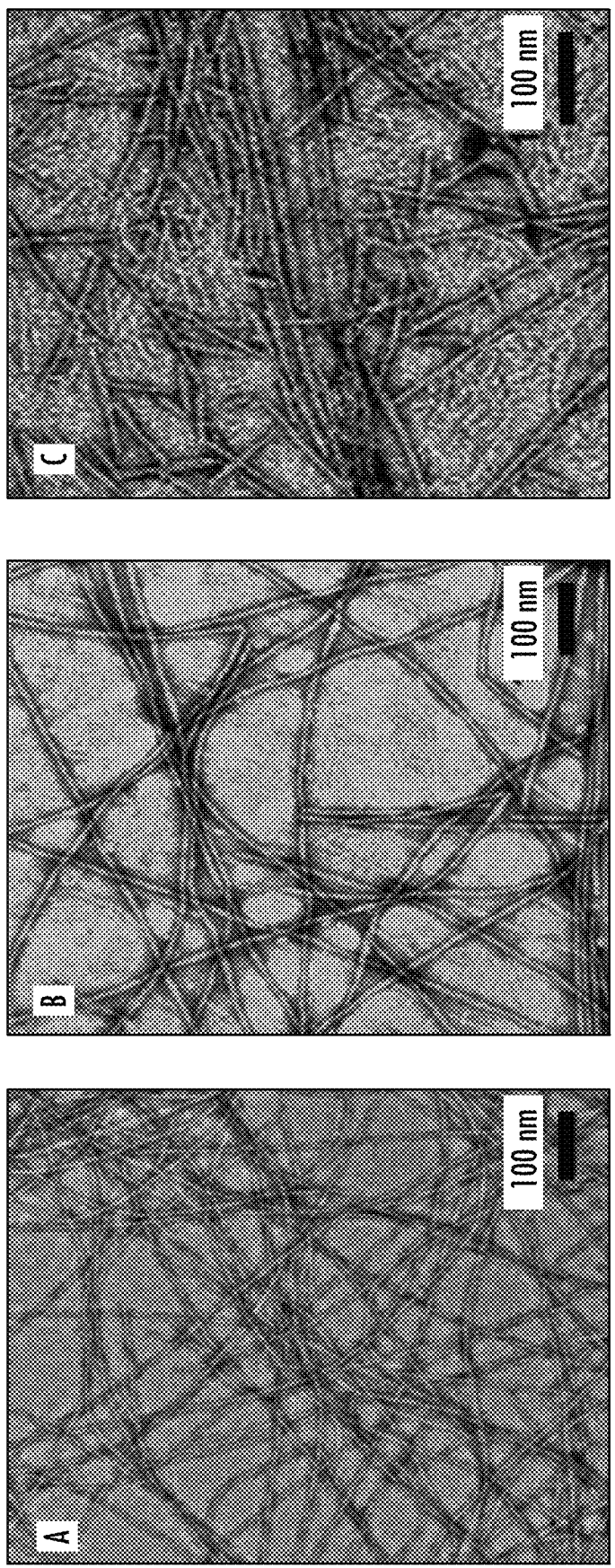

FIG. 20A-C. Representative TEM images of (20A) self-assembled C12-VVEE (SEQ ID NO: 10), (20B) self-assembled C12-VVKKGG (SEQ ID NO: 9) -Z33, and (20C) co-assembled nanofibers at 10:1 molar ratio of C12-VVEE (SEQ ID NO: 10) and C12-VVKKGG (SEQ ID NO: 9) -Z33.

Figure 21A:
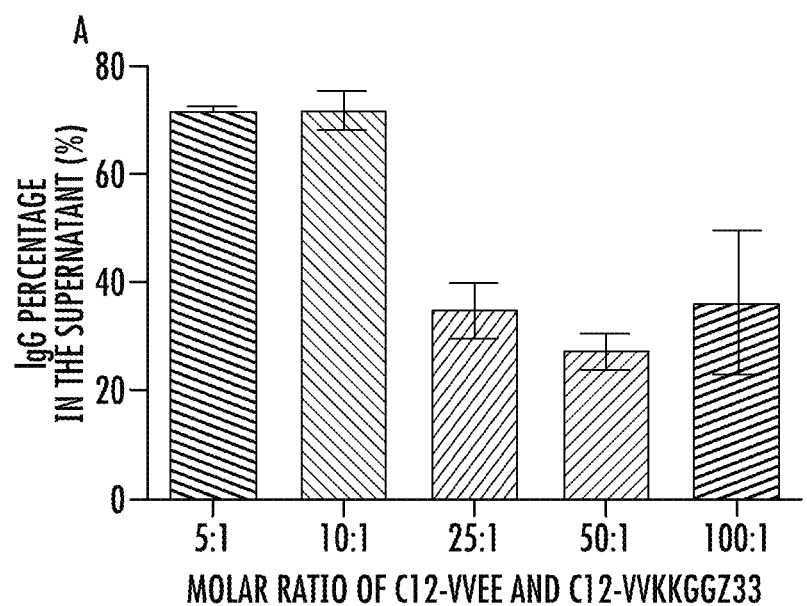
Figure 21B:
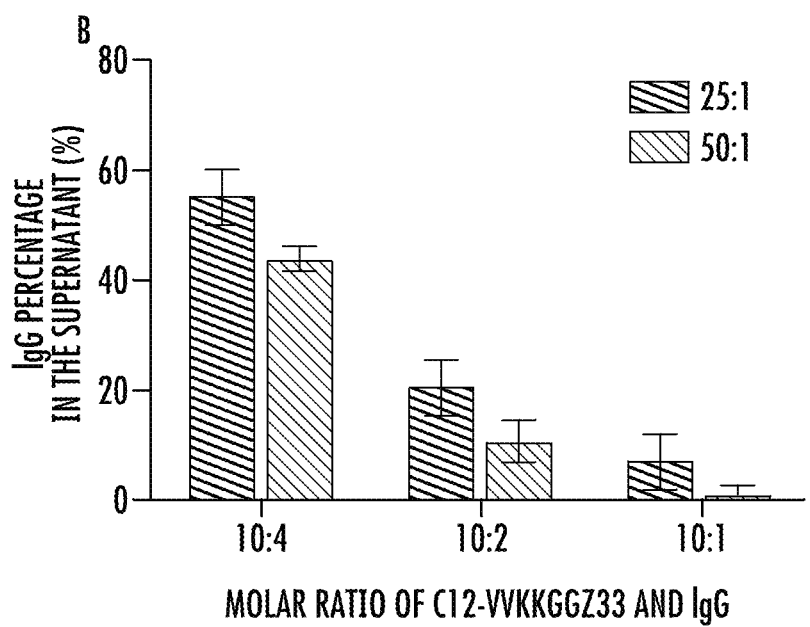

FIG. 21A-B. IgG binding and precipitation yield. (21A) IgG percentage in the supernatant of 20 μM IgG after incubation with C12-VVEE (SEQ ID NO: 10) and C12-VVKKGG(SEQ ID NO: 9) -Z33 at molar ratio of 5:1, 10:1, 25:1, 50:1, and 100:1 and subsequent addition of 1 M ammonium sulfate. Molar ratio of C12-VVKKGG (SEQ ID NO: 9) -Z33 and IgG: 10:2 (21B) IgG percentage in the supernatant of 20, 10, and 5 μM IgG after incubation with C12-VVEE (SEQ ID NO: 10) and C12-VVKKGG(SEQ ID NO: 9) -Z33 at molar ratio of 25:1 and 50:1 and subsequent addition of at 1 M ammonium sulfate. Molar ratios of C12-VVKKGG (SEQ ID NO: 9) -Z33 and IgG are 10:4, 10:2, and 10:1.

DETAILED DESCRIPTION OF THE INVENTION

Staphylococcal protein A (SPA) is a protein originally found in the cell wall of *Staphylococcus aureus*. It is composed of five homologous domains that fold into a three-helix bundle. Protein A plays an important role in immunology due to its specific binding to the Fc-portion of immunoglobulin G (aka IgG) from most mammalian species, including human Extensive structural and biochemical studies of protein A have been conducted. The first gene encoding SPA was cloned, sequenced and expressed in 1984, was followed by numerous synthetic and minimized IgG-binding domain based on protein A. Among them Z-58 domain is the first and most famous synthetic domain to be widely used in affinity chromatography and affinity precipitation. Another minimized binding domain, Z-33, was developed in 1996 without significantly changing the function of the molecule.

In accordance with several embodiments, the present invention provides methods for the modification and/derivatization of the amino acid sequence of the antibody binding domain into immuno-amphiphiles which serve as the building unit for IFs. Described herein are examples of the design and creation of IFs useful in binding IgG antibodies or portions or fragments thereof. Once IFs are formed in aqueous solution at physiological pH ranges, the exposed bioactive epitopes (binding sites) displayed on the surface are able to specifically bind IgG.

In accordance with an embodiment, the present invention self-assembling immunofibers comprising an immuno-amphiphile comprising an antibody binding peptide conjugated to a linear hydrocarbon chain.

In accordance with an embodiment, the present invention provides self-assembling immunofibers comprising one or more immuno-amphiphiles comprising an antibody binding peptide conjugated to a linear hydrocarbon chain and wherein the immuno-amphiphile has an α-helical conformation when in an aqueous solution at physiological pH.

In accordance with an embodiment, the present invention provides self-assembling immunofibers comprising one or more immuno-amphiphiles comprising an antibody binding peptide conjugated to a linear hydrocarbon chain, wherein the antibody binding peptide comprises a hydrophilic amino acid sequence from the Z33 peptide of Protein A of *Staphylococcus aureus*, or a functional portion or fragment or derivative thereof.

In accordance with an embodiment, the present invention provides self-assembling immunofibers comprising one or more immuno-amphiphiles comprising an antibody binding peptide conjugated to a linear hydrocarbon chain, wherein the antibody binding peptide comprises the amino acid sequence FNMQQQRRFYEALHDPNLNEEQRNAKIKSIRDD (SEQ ID NO: 1), or a functional portion or fragment or derivative thereof.

In accordance with an embodiment, the present invention provides self-assembling immunofibers comprising one or more immuno-amphiphiles comprising a fragment of an antibody binding peptide conjugated to a linear hydrocarbon chain.

In accordance with an embodiment, the present invention provides self-assembling immunofibers comprising one or more immuno-amphiphiles comprising a fragment of an antibody binding peptide conjugated to a linear hydrocarbon chain and wherein the immuno-amphiphile has an α-helical conformation when in an aqueous solution at physiological pH.

In accordance with an embodiment, the present invention provides self-assembling immunofibers comprising one or more immuno-amphiphiles comprising a fragment of an antibody binding peptide conjugated to a linear hydrocarbon chain and wherein the immuno-amphiphile has an β-sheet conformation when in an aqueous solution at physiological pH.

In accordance with an embodiment, the present invention provides self-assembling immunofibers comprising one or more immuno-amphiphiles comprising a fragment of an antibody binding peptide conjugated to a linear hydrocarbon chain, wherein the antibody binding peptide has a portion of the hydrophilic amino acid sequence of the Z33 peptide of Protein A of *Staphylococcus aureus.*

As used herein, the term "a fragment of an antibody binding peptide" means a portion or fragment of the Z33 peptide of Protein A of *Staphylococcus aureus* that has fewer than the 33 amino acids of SEQ ID NO: 1. In some embodiments, the term "a fragment of an antibody binding peptide" means a portion of the Z33 peptide comprising a peptide having at least one α-helical region within the peptide. The fragment of an antibody binding peptide can also comprise additional amino acids that may or may not comprise an α-helical region.

In accordance with an embodiment, the present invention provides an immuno-amphiphile comprising a fragment of an antibody binding peptide conjugated to a linear hydrocarbon chain wherein the fragment of an antibody binding peptide comprises the amino acid sequence of FNMQQQRRFYEALHD (SEQ ID NO: 2) and is referred to as Helix 1. In some embodiments, Helix 1 comprises the amino acid sequence of FNMQQQRRFYEALHDK (SEQ ID NO: 3). In another embodiment, Helix 1 comprises the amino acid sequence of FNMQQQRRFYEALHDKK (SEQ ID NO: 4).

In accordance with an embodiment, the present invention provides an immuno-amphiphile comprising a fragment of an antibody binding peptide conjugated to a linear hydrocarbon chain wherein the fragment of an antibody binding peptide comprises the amino acid sequence of PNLNEEQRNAKIKSIRDD (SEQ ID NO: 5) and is referred to as Helix 2. In some embodiments, Helix 2 comprises the amino acid sequence of FPNLNEEQRNAKIKSIRDD (SEQ ID NO: 6).

As used herein, the term "immuno-amphiphiles" means a molecule that can spontaneously associate into discrete, stable supramolecular nanostructures termed "immunofibers" (IFs). Generally, the IFs of the present invention can assemble in a pH range between about 2.8 to about 7.5. However, the binding properties are also pH dependent. Those IFs which are more positively charged are easier to associate with higher pH solutions, and conversely, negatively charged IFs will associate easier in lower pH solutions.

In some embodiments, the immuno-amphiphiles of the present invention comprise a hydrophilic peptide is conjugated to a hydrocarbon chain having between 8 and 22 carbons, and the chain can be linear or branched. There is an upper limit to the number of carbons in view of solubility in an aqueous solution. The hydrophilic peptide increases the aqueous solubility of the nanostructure and can promote the formation of well-defined nanostructure architectures including, but not limited to, cylindrical or spherical micelles, hollow nanotubes, toroids, discs and vesicles, through preferred secondary structure formation, e.g. beta sheet, alpha helix, poly proline type-II helix, beta turn.

As used herein, the term "hydrocarbon chain" means is synonymous with the term "aliphatic chain," which is an art-recognized term and includes linear, branched, and cyclic alkanes, alkenes or alkynes. In certain embodiments, aliphatic groups in the present invention are linear or branched and have from 8- about 22 carbon atoms.

The term "alkyl" is art-recognized, and its use herein includes saturated aliphatic groups, including straight-chain alkyl groups and branched-chain alkyl groups.

As used herein, the term "antibody binding peptide" means a peptide that has the ability to bind an antibody, or a specific portion of an antibody molecule, for example, the Fc portion, with high specificity, such as having a $K_d$ of between about $10^{-6}$ M to about $10^{-10}$ M.

In some embodiments, the antibody binding peptide is the hydrophilic amino acid sequence of the Z33 two-helix derivative peptide of the Z-domain of Protein A of *Staphylococcus aureus*, or a functional portion or fragment or derivative thereof.

As used herein, the Z33 peptide of Protein A has the amino acid sequence of FNMQQQRRFYEALHDPNLNE-EQRNAKIKSIRDD (SEQ ID NO: 1).

In some embodiments, the antibody binding peptide is a fragment of the Z33 peptide of Protein A conjugated to a linear hydrocarbon chain wherein the fragment of an antibody binding peptide comprises the amino acid sequence of FNMQQQRRFYEALHD (SEQ ID NO: 2) and is referred to as Helix 1. In some embodiments, Helix 1 comprises the amino acid sequence of FNMQQQRRFYEALHDK (SEQ ID NO: 3). In another embodiment, Helix 1 comprises the amino acid sequence of FNMQQQRRFYEALHDKK (SEQ ID NO: 4).

In some embodiments, the antibody binding peptide is a fragment of the Z33 peptide of Protein A conjugated to a linear hydrocarbon chain, wherein the antibody binding peptide comprises the amino acid sequence of PNLNEEQR-NAKIKSIRDD (SEQ ID NO: 5) and is referred to as Helix 2. In some embodiments, Helix 2 comprises the amino acid sequence of FPNLNEEQRNAKIKSIRDD (SEQ ID NO: 6).

In accordance with another embodiment, the present invention provides a an immunofiber composition comprising one or more immuno-amphiphiles comprising an antibody binding peptide conjugated to a linear hydrocarbon chain, wherein the antibody binding peptide has a hydrophilic amino acid sequence of the Z33 peptide of Protein A of Staphylococcus aureus, or a functional portions or fragments or derivatives thereof. In some embodiments, the functional portion or fragments or derivatives are selected from the group consisting of SEQ ID NOS: 1-6.

It will be understood by those of ordinary skill in the art that other binding peptides can be substituted for the Z33 peptide to bind other proteins. For example, streptavidin or a function portion or fragment thereof could be incorporated in the immuno-amphiphiles and the resulting IFs could be used to bind biotinylated compounds.

The term, "amino acid" includes the residues of the natural α-amino acids (e.g., Ala, Arg, Asn, Asp, Cys, Glu, Gln, Gly, His, Lys, Ile, Leu, Met, Phe, Pro, Ser, Thr, Trp, Tyr, and Val) in D or L form, as well as β-amino acids, synthetic and non-natural amino acids. Many types of amino acid residues are useful in the polypeptides and the invention is not limited to natural, genetically-encoded amino acids. Examples of amino acids that can be utilized in the peptides described herein can be found, for example, in Fasman, 1989, CRC Practical Handbook of Biochemistry and Molecular Biology, CRC Press, Inc., and the reference cited therein. Another source of a wide array of amino acid residues is provided by the website of RSP Amino Acids LLC.

Reference herein to "derivatives" includes parts, fragments and portions of the inventive antibody binding peptides of the present invention. A derivative also includes a single or multiple amino acid substitution, deletion and/or addition. Homologues include functionally, structurally or sterochemically similar peptides from venom from the same species of snake or from within the same genus or family of snake. All such homologues are contemplated by the present invention.

Analogs and mimetics include molecules which include molecules which contain non-naturally occurring amino acids or which do not contain amino acids but nevertheless behave functionally the same as the peptide. Natural product screening is one useful strategy for identifying analogs and mimetics.

Examples of incorporating non-natural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, omithine, sarcosine, 4-amino-3-hydroxy-6-methylheptanoic acid, 2-thienyl alanine and/or D-isomers of amino acids. A partial list of known non-natural amino acid contemplated herein is shown in Table 1.

TABLE 1

| Non-natural Amino Acids | |
|---|---|
| Non-conventional amino acid | Code |
| α-aminobutyric acid | Abu |
| α-amino-α-methylbutyrate | Mgabu |
| aminocyclopropane-carboxylate | Cpro |
| aminoisobutyric acid | Aib |
| aminonorbomyl-carboxylate | Norb |
| cyclohexylalanine | |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |

TABLE 1-continued

Non-natural Amino Acids

| Non-conventional amino acid | Code |
|---|---|
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl) carbamylmethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| Chexa L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl)glycine | Nnbhe |

Analogs of the subject peptides contemplated herein include modifications to side chains, incorporation of non-natural amino acids and/or their derivatives during peptide synthesis and the use of crosslinkers and other methods which impose conformational constraints on the peptide molecule or their analogs.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The term, "peptide," as used herein, includes a sequence of from four to 100 amino acid residues in length, preferably about 10 to 80 residues in length, more preferably, 15 to 65 residues in length, and in which the α-carboxyl group of one amino acid is joined by an amide bond to the main chain (α- or β-) amino group of the adjacent amino acid.

In accordance with some embodiments, generally, the present invention provides methods for purification of proteins or peptides of interest wherein the proteins or peptides are capable of being bound by the antibody binding peptide portion of the immunofiber using immunoprecipitation methods with the immunofibers of the present invention.

In accordance with an embodiment, the present invention provides a method for purification of peptides or proteins having an Fc portion of an immunoglobulin molecule, or a functional portion or fragment thereof, comprising contacting a solution at a first pH level containing one or more peptides or proteins of interest with an immunofiber composition comprising one or more immuno-amphiphiles, wherein the one or more immuno-amphiphiles comprise an Fc binding peptide conjugated to a hydrocarbon chain, and wherein the Fc binding peptide has a hydrophilic amino acid sequence of the Z33 peptide of Protein A of Staphylococcus aureus, or a functional portion or fragment or derivative thereof; allowing the one or more proteins of interest to bind the Fc binding peptide or a functional portion or fragment or derivative thereof; changing the pH level of the solution to a pH which causes a change in the conformation of the Fc binding peptide to a conformation which no longer binds the one or more proteins of interest; and extracting the released one or more proteins of interest from the solution.

Generally, Fc containing proteins can be immunoglobulins or antibodies (IgG type, for example) or fusion peptides or proteins containing an Fc portion, are purified by mixing the proteins in a sample with the immunofibers of the present invention in an aqueous solution and a physiological pH, and allowing the immunofibers to bind the Fc portion of the protein molecule of interest. In some embodiments, the immunofibers comprise the Z33 portion of Protein A and are specific for the Fc portion of IgG molecules or fusion peptides or proteins comprising them.

In accordance with some other embodiments, the immunofibers are then separated from bound proteins using various filtration methods, such as, for example diafiltration, microfiltration or ultrafiltration.

In an embodiment the immunofibers compositions of the present invention comprise two or more fragments of the Z33 peptide of Protein A conjugated to a linear hydrocarbon. In an embodiment, the immunofibers used in the methods of purification or binding of antibodies can comprise a mixture of Helix 1 and Helix 2 peptides. For example the methods can comprise addition of one or more Helix 1 peptides having a peptide sequence of SEQ ID NOS: 2-4, and combinations thereof, and the addition of one or more Helix 2 peptides having a peptide sequence of SEQ ID NO: 5 or 6, and combinations thereof.

After a period of time to allow the immunofibers to bind, the immunofibers form immunofibers-protein complexes in solution. The complexes formed can then be separated from the unbound fibers and proteins and other components in the sample by many known separation means, including, for example, salt-induced precipitation and centrifugation. The separated complexes can then be introduced into another solution at an acidic pH, where the immunofibers lose their binding affinity for the proteins. The proteins can then be separated from the dissociated immunofibers by filtration, such as diafiltration or other means, and the dissociated monomers can be removed as well.

It is contemplated that the immunofibers of the present invention can be used with other protein purification methods, such as covalently immobilizing them onto porous resins (such as beaded agarose) or magnetic beads, or combinations of immobilized substrates and immunoprecipitation methods.

As used herein, the term "sample" means any sample or solution or fluid containing an antibody of interest which can be bound using the immunofibers of the present invention. In some embodiments, the sample can be a biological sample.

In accordance with one or more embodiments of the present invention, it will be understood that the term "biological sample" or "biological fluid" includes, but is not limited to, any quantity of a substance from a living or formerly living patient or mammal Such substances include, but are not limited to, blood, serum, plasma, urine, cells, organs, tissues, bone, bone marrow, lymph, lymph nodes, synovial tissue, chondrocytes, synovial macrophages, endothelial cells, and skin.

All the sequences, CMCs, and secondary structures of IAs in this study are summarized in Table 1. Both long single-chain and double-chain alkylation can lead to the formation of one-dimensional filaments, but differ in morphology, CMC, and secondary structures. The length and number of alkyl chains have been proven to affect the self-assembly behavior of the peptide conjugates. For example, Jan van Hest and coworkers found that the GANPNAAG (SEQ ID NO: 8) peptide conjugated with C12 or shorter alkyl chains showed no aggregates. However, fibrous aggregates and tubular structures were found in C14 conjugates and C16 or longer conjugates, respectively. Similarly, as reported by other researchers previously, the CMC of the single-chain alkylated amphiphiles decreases as the length of alkyl chain increases, due to the enhanced hydrophobicity that promotes the aggregation of IAs. Alkyl chain conjugation was previously demonstrated to enhance the stability of α-helix secondary structures and increase in content in the conjugated form. Enhanced bioactivities in some α-helix for forming peptide were reported. For example, an increase in bactericidal activity for SC4 peptide-amphiphiles was found by Mayo and Tirell. Our results seem to conflict with the system investigated by Forns and co-workers, where helicity of a 16-residue peptide increases as the alkyl chains enlongates. However, this discrepancy may be caused by the pre-existed α-helix structures in the unconjugated 16-residue peptide. Mihara and co-workers found that longer N-terminal alkylated 2α-helix peptide underwent a higher rate of α-to-β transitions, indicating the formation of β-sheets promoted by long alkyl chains.

In conclusion, two series of immuno-amphiphiles were successfully designed and synthesized. Through different molecular design of the IAs, it was found different ways of alkylation led the IA molecules to vary in several self-assembly properties such as the CMC value, morphology and component of secondary structures. Our results clearly show that both single-chain and double-chain alkylation can lead to the formation of one-dimensional filaments. The longer single alkyl chain was able to promote the aggregation of the IA molecules and increase the formation of β-sheet. Double-chain alkylation could help the formation of α-helix in the self-assembled filaments. However, there are variations in the impact of alkylation among different peptide molecules. This strategy of tuning the length and number of alkyl chains can be further developed and applied in other self-assembled functional peptide system that requires specific secondary structure to exert desired bioactivities.

In accordance with some embodiments, the alkyl chains used to alkylate the peptides and fragments thereof, can have carbon lengths of two to twenty four carbons in length, including intermediate lengths of 3, 4, 5, 6, 7, 8, 10, 12, 14, 16, 18, 20, 22 and 24 carbons in length. Additionally, the peptides or fragments thereof can have 1 to 4 alkyl chains alkylated to the peptide or fragment thereof.

An Alternative Embodiment of the Immunofiber Compositions of the Present Invention.

The inventor's previous work showed high IgG binding affinity and potential IgG precipitation ability of self-assembling C12-Z33 iniinunofibers. Considering the tight packing of C12-Z33 in immunofibers, a disadvantage of the first immunofiber design described above is there might be limited ligand accessibility of the Z33 ligand for IgG molecules with diameter of 10 nm. Although high density of Z33 ligands are presented at the surface of immunofibers, it was thought that steric hindrance could prevent the IgG binding efficiency and the crosslinking of immunofibers to form large assemblies for precipitation. As such, an alternative embodiment of the immunofiber compositions of the present invention is provided.

In accordance with one or more embodiments, an improved immunofiber binding system is provided by combining binding molecules (alkyl-XXYYZZ-antibody binding peptide) and spacer molecules (alkyl-XXBB) in a co-assembled immunofiber system, wherein the first spacer peptide comprises the generic sequence of XXYYZZ, wherein XX is two amino acids having a small hydrophobic side chain and can be the same or different amino acid, YY is two amino acids having a positively charged side chain and can be the same or different amino acid, and ZZ is two amino acids having a small neutral side chain and can be the same or different amino acid, and further comprising an immunofiber spacer molecule having a linear hydrocarbon chain at its N-terminus conjugated to a peptide sequence comprising the generic sequence of XXBB, wherein XX is two amino acids having a small hydrophobic side chain and can be the same or different amino acid, and wherein BB is two amino acids having a negatively charged side chain, and can be the same or different amino acid.

In an exemplary embodiment, the immunofiber binding molecule contains between 4-8 amino acids, and in some embodiments, 6 amino acids residues comprising VVKKGG (SEQ ID NO: 9) between the carbon chain and antibody binding peptide Z33 compared to the above provided C12-Z33 immunofiber. Two hydrophobic amino acids such as valine (VV) promotes the formation of one-dimensional structures. Two positively charged amino acids such as glutamic acid (EE)were designed as the hydrophilic segment in the spacer molecule and two negatively charged amino acids such as lysine (KK) were designed accordingly for electrostatic interactions between positive charged and negative charged amino acids and thus inducing the alternating packing of the binding and spacer immunofibers molecules C12-VVKKGG (SEQ ID NO: 9) -Z33. Two neutral amino acids such as glycine (GG) were designed for further separating antibody binding peptide, such as Z33 from the alkyl chains. When dissolving the binding and spacer molecules in aqueous solution, it was expected that these two molecules can homogeneously co-assemble into one-dimensional immunofibers with the binding ligand Z33 sticking out on the surface (FIG. 19).

In accordance with a further embodiment, the present invention provides an immunofiber composition comprising an immunofiber binding molecule comprising an antibody binding peptide conjugated to a linear hydrocarbon chain at its N-terminus, and conjugated to a first spacer peptide conjugated to an antibody binding peptide having a hydrophilic amino acid sequence of the Z33 peptide of Protein A of *Staphylococcus aureus*, or functional portions or fragments or derivatives thereof at its C-terminus, and wherein the first spacer peptide comprises the generic sequence of XXYYZZ, wherein XX is two amino acids having a small hydrophobic side chain and can be the same or different amino acid, YY is two amino acids having a positively charged side chain and can be the same or different amino acid, and ZZ is two amino acids having a small neutral side chain and can be the same or different amino acid, and further comprising an immunofiber spacer molecule having a linear hydrocarbon chain at its N-terminus conjugated to a peptide sequence comprising the generic sequence of XXBB, wherein XX is two amino acids having a small hydrophobic side chain and can be the same or different amino acid, and wherein BB is two amino acids having a negatively charged side chain, and can be the same or different amino acid. For example, the amino acid sequence VVEE (SEQ ID NO: 10) can be used to prepare C12-VVEE (SEQ ID NO: 10) as the immunofiber spacer peptide.

It will be understood by those of ordinary skill in the art, that the term "amino acids with a hydrophobic side chain" means amino acids such as Ala, Val, Ile, Leu. The term "amino acids with a positively charged side chain" means Arg, His and Lys. The term amino acids with a small neutral side chain" means amino acids such as Gly or Pro. The term "amino acids with a negatively charged side chain" means amino acids such as Asp or Glu.

The immunofiber compositions and alternative immunofiber binding systems comprising the immunofiber binding molecules (alkyl-XXYYZZ-antibody binding peptide) and spacer molecules (alkyl-XXBB) of the present invention are useful in purifying antibodies and other molecules comprising an Fc portion of an antibody or portion or fragment thereof. In some embodiments, the immunofiber compositions of the present invention can be used to separate or purify any peptide or fusion protein which comprises at least a portion of the Fc of an antibody molecule.

The removal of last impurity traces from a purified protein is generally called polishing. It is an important step in downstream processing since protein impurities may generate undesirable side effects when the preparation is intended for research, diagnostic and more importantly therapeutic applications. Polishing is generally achieved by using orthogonal separation methods to previous steps, the most common being gel permeation chromatography. In spite of its polishing effectiveness, this technique suffers from a poor separation capacity and modest productivity as a result of low speed. Other approaches, for instance, based on anion exchange or on hydrophobic chromatography, that may be optimized for a given process cannot be used as generic methods. In some embodiments, additional polishing steps will be used to purify the proteins of interest.

Thus, in view of the foregoing, the present invention provides methods for purification of antibodies or Fc containing peptides or proteins comprising the steps of: a) dissolving a sample containing any of the immunofiber compositions described above in an aqueous solution and a physiological pH and aging overnight to make it self-assemble into IFs; b) mixing a sample containing antibodies with the IFs solution, and allowing the IFs to bind the Fc portion of the immunoglobulin molecule or Fc containing peptides or proteins and form an immunofiber-Fc immunoglobulin or immunofiber-Fc containing peptide or protein complex in solution; c) separating the immunofiber-Fc immunoglobulin or immunofiber-Fc containing peptide or protein complex from the solution by adding salt and centrifugation; d) dissociating the IFs from the immunoglobulins or Fc containing peptides or proteins and collecting the unbound immunoglobulins or Fc containing peptides or proteins.

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

EXAMPLES

Materials. All Fmoc amino acids and resins were purchased from Advanced Automated Peptide Protein Technologies (AAPPTEC, Louisville, KY, UXSA), and Fmoc-Lys(Fmoc) were obtained from Novabiochem (San Diego, CA, USA). The therapeutic human IgG1 (IgG1) was obtained from Bristol-Myers Squibb (Boston, MA, USA), and IgG elution buffer was sourced from Thermo Fisher Scientific (Rockford, IL, USA). All other reagents were obtained from VWR (Radnor, PA, USA) and used as received without further purification.

Molecular Synthesis. C12-Z33 and 2C8-Z33 immunoamphiphiles were synthesized using similar methods. In brief, Z33 peptide were first synthesized on the Focus XC automatic peptide synthesizer (AAPPTEC, Louisville, KY) using standard 9-fluorenylmethoxycarbonyl (Fmoc) solid phase synthesis protocols. C12 (or 2C8) alkyl chain was then manually coupled at the N-terminus (after Fmoc removal) of Z33 peptide with lauric acid (or octanoic acid)/HBTU/DIEA at a ratio of 4 (or 8): 4: 6 relative to the Z33 peptide, shaking overnight at room temperature. Other alkyl chains were manually coupled at the N-terminus of the peptide or the side chain of lysine (K) to produce different IAs, and shaked overnight at room temperature. Fmoc deprotections were performed using a 20% 4-methylpiperidine in DMF solution for 10 minutes, repeating once. In all cases, reactions were monitored by the ninhydrin test (Anaspec Inc., Fremont, CA) for free amines Completed peptides were cleaved from the solid support using a mixture of TFA/TIS/H2O in a ratio of 92.5:5:2.5 for 2.5 hours. Excess TFA was removed by rotary evaporation and cold diethyl ether was added to precipitate the crude peptide. By centrifugation method, precipitated peptide and diethyl ether were separated at 6000 rpm for 3 minutes. Peptides were washed another 2 times with diethyl ether and solution was removed by centrifugation.

Molecular Synthesis of IAs with fragment of antibody binding peptides. Peptide amphiphiles were synthesized using similar methods. Below we take Helix1-C16, Helix1-2C8, C16-Helix2, and 2C8-Helix2 as examples to show the synthesis process. In brief, FNMQQQRRFYEALHDK (Helix1+Kmtt) (SEQ ID NO: 3) and FNMQQQRRF-YEALHDKK (Helix1+Kmtt+Kmtt) (SEQ ID NO: 4) peptide sequences were first synthesized on the Focus XC automatic peptide synthesizer (AAPPTEC, Louisville, KY) using standard 9-fluorenylmethoxycarbonyl (Fmoc) solid phase synthesis protocols. The K-methylthiotetrazole (Kmtt) was added at the C-terminus of Helix1 sequence for further reaction. Palmitic acid (C16) or octanoic acid (2C8) alkyl tails were then manually coupled at the side chain of Kmtt in Helix1+Kmtt and Helix1+Kmtt+Kmtt respectively to produce Helix1-C16 and Helix1-2C8, and shaked overnight at room temperature. Similarly, for C16-Helix2, and 2C8-Helix2, PNLNEEQRNAKIKSIRDD (Helix2) (SEQ ID NO: 5) and FPNLNEEQRNAKIKSIRDD (K-Fmoc-Helix2) (SEQ ID NO: 6) peptide sequences were first synthesized on the Focus XC automatic peptide synthesizer. The K-Fmoc was added at the N-terminus of Helix2 sequence for further reaction. Palmitic acid (C16) or octanoic acid (2C8) alkyl tails were then manually coupled at the N-terminus in Helix2 or both the N-terminus and side chain of K-Fmoc in K-Fmoc-Helix2 respectively to produce Helix1-C16 and Helix1-2C8, shaking overnight at room temperature. Fmoc deprotections were performed using a 20% 4-methylpiperidine in DMF solution for 10 minutes, repeated once. In all cases, reactions were tested using the ninhydrin test (Anaspec Inc., Fremont, CA) for free amines Completed peptides were cleaved from the solid support using a mixture of TFA/TIS/$H_2O$ in a ratio of 92.5:5:2.5 for 2.5 hours. Excess TFA was removed by rotary evaporation and cold diethyl ether was added to precipitate the crude peptide. By centrifugation method, precipitated peptide and diethyl ether were separated at 6000 rpm for 3 minutes. Peptides were washed 2 more times with diethyl ether and the solution was removed by centrifugation.

The IAs were purified by preparative RP-HPLC using a Varian Polymeric Column (PLRP-S, 100 Å, 10 μm, 150×25 mm) at 25° C. on a Varian ProStar Model 325 preparative HPLC (Agilent Technologies, Santa Clara, CA) equipped with a fraction collector. A water/acetonitrile gradient containing 0.1% v/v TFA was used as eluent at a flow rate of 20 mL/min. The absorbance peak was monitored at 220 nm for Z33 peptide segments. The crude materials were dissolved in 20 ml of 0.1% aqueous TFA, and each purification run was carried out with a 10 ml injection. Collected fractions were analyzed MALDI-ToF (BrukerAutoflex III MALDI-ToF instrument, Billerica, MA) and those containing the desired product were lyophilized (FreeZone −105° C. 4.5 L freeze dryer, Labconco, Kansas City, MO) and stored at −30° C.

Self-Assembly of Immuno-Amphiphiles and TEM Imaging Immuno-amphiphiles with 1 mM concentration were pretreated with HFIP and then dissolved in 1×PBS or deionized water and aged overnight at room temperature; 10 μL of 10 fold diluted sample was spotted on a carbon film copper grid with 400 square mesh (from EMS: Electron Microscopy Sciences) and the excess was removed with filter paper to leave a thin film of sample on the grid. After letting the sample dry for 5 minutes, 10 μL of 2% uranyl acetate was added to sample grid, and the excess was removed after 30 seconds. All samples were dried for at least 3 hours before TEM imaging.

Circular Dichroism Spectroscopy (CD). The CD experiments of self-assembled IA samples were conducted on a Jasco J-710 spectropolarimeter (JASCO, Easton, MD, USA) using a 1 mm path length quartz UV-Vis absorption cell (ThermoFisher Scientific, Pittsburgh, PA, USA) at 25° C. The samples were instantly diluted from the 1 mM stock solution to 100 μM in 1×PBS prior to the experiment. The spectra were collected in the wavelength range of 190-280 nm as the average of three scans. A background spectrum of the solvent was acquired and subtracted from the sample spectrum. Collected data was normalized with respect to sample concentration.

ITC Experiment. Isothermal titration calorimetry experiments were performed on the C12 and 2C8 IAs using a high precision VP-ITC titration calorimetric system (Microcal Inc.). The IgG1 solution was titrated with immuno-amphiphiles in 1×PBS (pH 7.4 or 2.8) at 15° C. The IgG1 concentration was calculated using the mass extinction coefficient of 1.4 at 280 nm for a 0.1% (1 mg/ml) IgG solution. The concentration of immune-amphiphiles was determined by total nitrogen assay (Anal. Biochem., 61.2 (1974): 623-627). The heat evolved after each injection was obtained from the integral of the calorimetric signal. The heat associated with the binding of immuno-amphiphiles to IgG1 was obtained by subtracting the heat of dilution. Analysis of the data was performed using MicroCal Origin™ package.

CMC Measurement. The CMC of the Z33 fragment IAs with fragmented antibody binding peptides was determined by incubating these molecules at various concentrations with a certain amount of Nile Red. The stock solution of Nile Red was initially prepared by dissolving the dye in acetone at 50 μM. 10 μL stock solution was loaded into several centrifuge tubes, where the solvent evaporates under room temperature to yield the dry mass of Nile Red. Various concentrations of the peptide solutions were prepared in deionized water, and then identical volume was added into the centrifuge tubes containing dry Nile Red and aged overnight. Fluorescent spectra of Nile Red were then monitored by a Fluorolog fluorometer (Jobin Yvon, Edison, NJ) with fixed excitation wavelength at 560 nm; emission spectra were monitored 580-720 nm. The CMC of IAs is determined by a blue-shift of the emission maximum, whereas this transition occurs as the incubated peptides exceed their CMC values.

Thioflavin T (ThT) Spectroscopic Assay. A ThT stock solution was prepared in deionized water at 50 μM. 100 μM Z33 IAs with fragmented antibody binding peptides were vortexed and incubated with identical volume of ThT stock solution for 1 h. The fluorescence intensity was then measured by a Fluorolog fluorometer (Jobin Yvon, Edison, NJ) with excitation at 440 nm (slit width 5 nm) and emission at 482 nm (slit width 10 nm).

Molecular Design of full length Z33 immuno-amphiphiles. The construction of this amphiphilic peptide conjugates such as peptide amphiphiles, peptide-polymer conjugates, peptide-drug conjugates, etc., has been widely used to create a variety of supramolecular nanostructures. IgG binding immuno-amphiphiles consisting of hydrophilic Z33 peptide sequence (FNMQQQRRFYEALHDPNLNEEQRNAKIKSIRDD) (SEQ ID NO: 1) and hydrophobic alkyl chains were designed to serve as the building motifs for immuno-fibers (IFs). Z33 peptide is a two-helix derivative from protein A (FIG. 1A) that specifically binds to the Fc portion of IgG with high binding affinity (Kd=43 nM).

Two IAs, C12-Z33 and 2C8-Z33 (FIG. 1B), were synthesized via directly conjugating a lauric acid moiety (C12), or two octanoic acid moieties (2C8), onto the N-terminus of Z33 peptide. As is shown in FIG. 1C, the IAs were expected to self-assemble into IFs and specifically bind to IgG from the antibody mixture solution. Pure Z33 peptide was also synthesized to compare the bioactivity between Z33 molecule and Z33 containing IFs. Another control molecule C12-SZ33 was designed by conjugating C12 on to the N-terminus of Z33 with scrambled sequence. All the molecules were synthesized and purified using automated solid-phase peptide synthesis (SPPS) methods and RP-HPLC. The purity and expected molecular masses of the synthesized compounds were confirmed using analytical HPLC and mass spectrometry.

Example 2

Figures 2A, 2B, 2C, 2D, 2E, 2F:
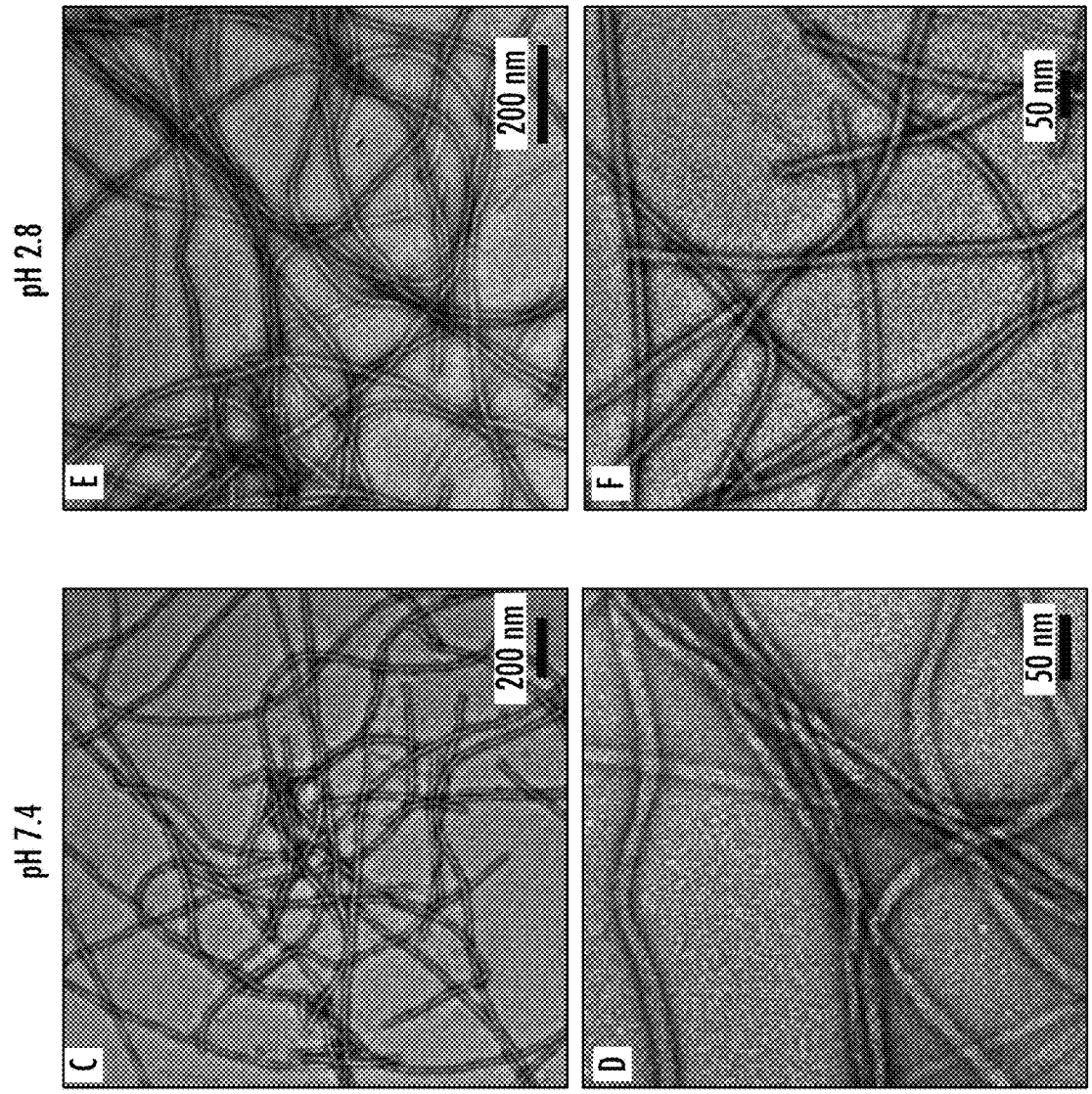
Figures 4A, 4B, 4C, 4D, 4E:
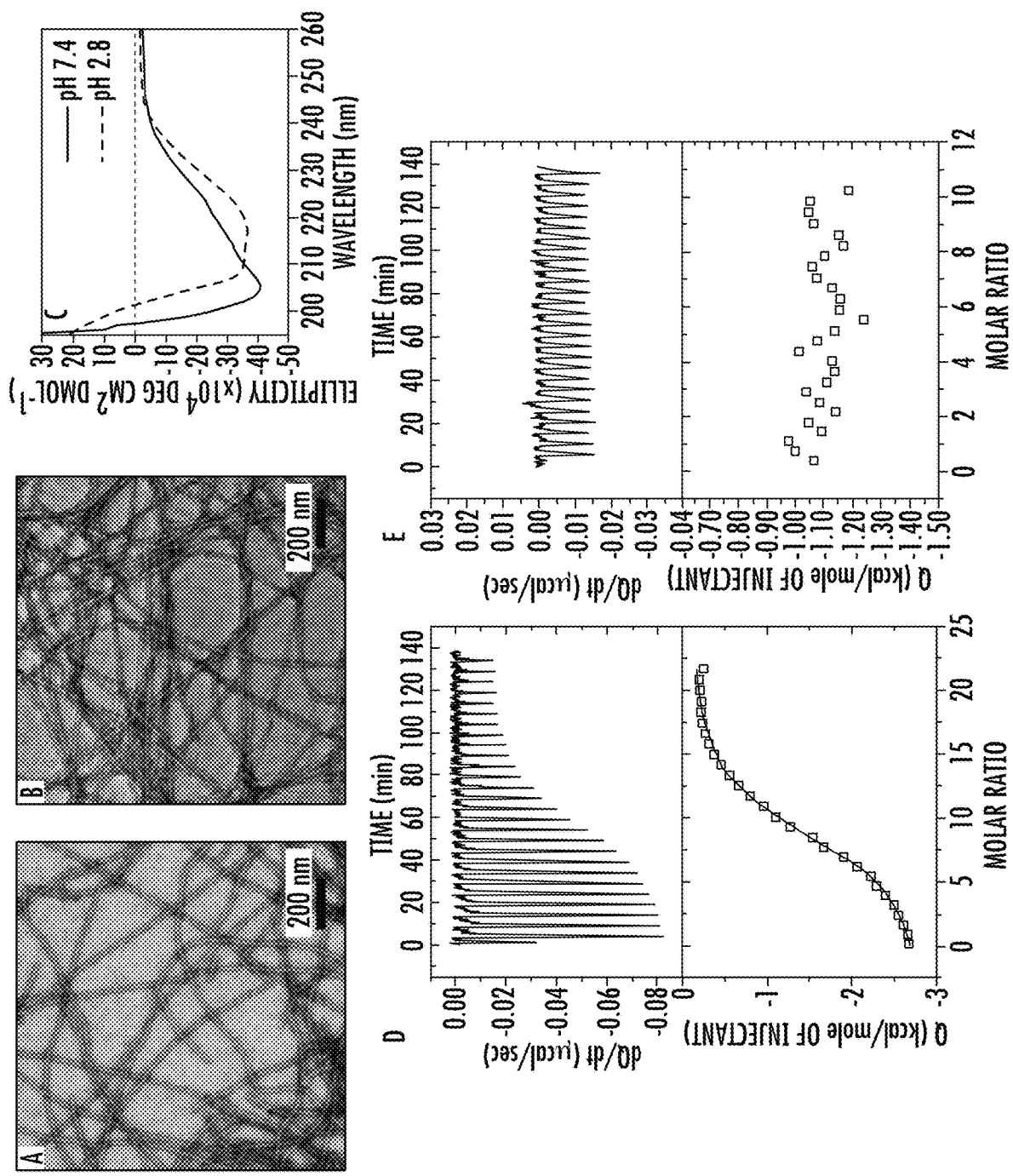
Figures 5A, 5B, 5C, 5D:
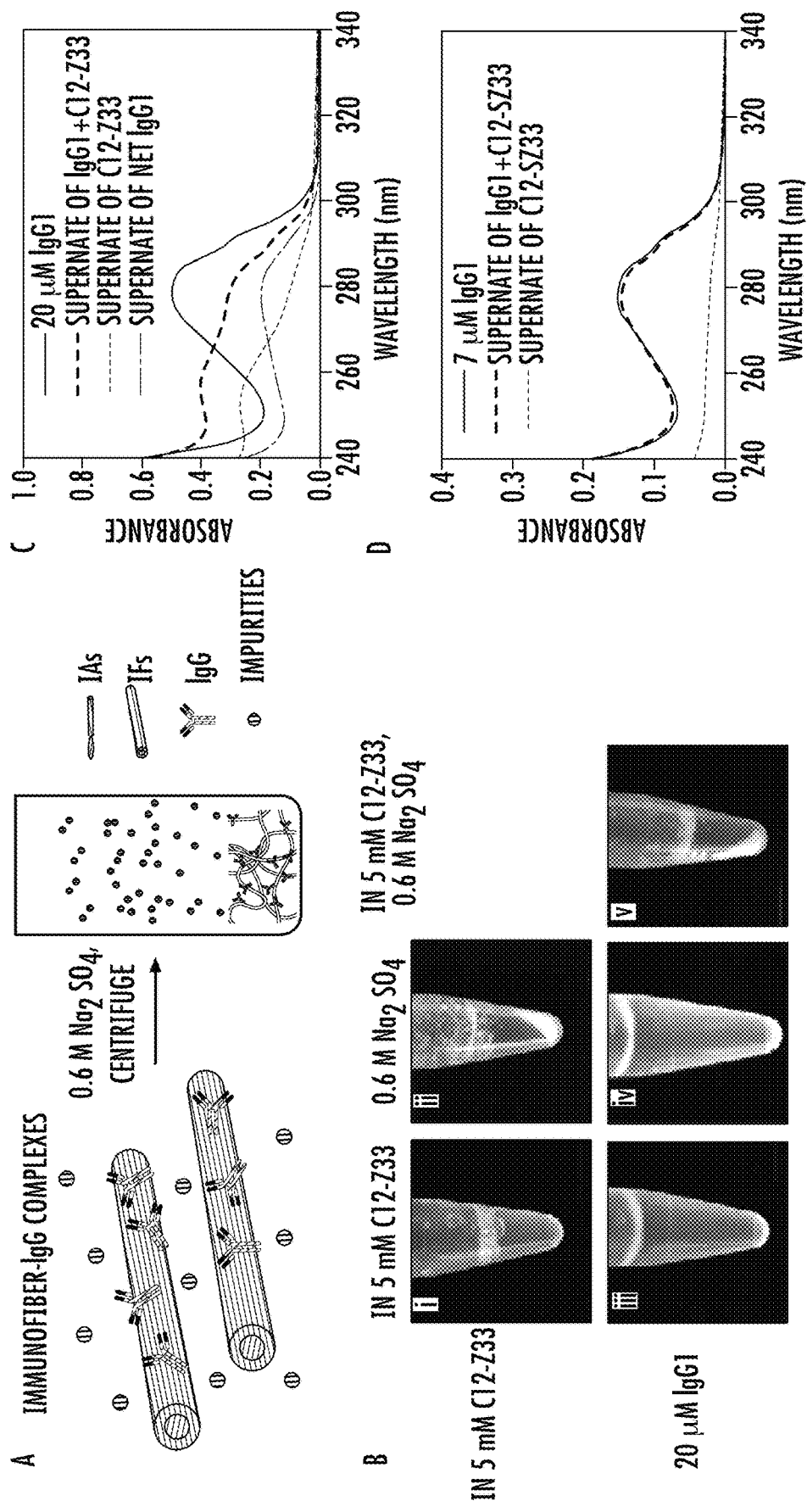

Molecular Self-Assembly and Characterization of full length Z33 immuno-amphiphiles. The self-assembly of two IAs can be easily achieved through a two-step operation. First, the IAs were pretreated in hexafluoroisopropanol (HFIP) separately to eliminate any pre-existing nanostructures that may affect its solubility and the uniformity of the self-assembled morphologies. Second, HFIP were removed via evaporation, followed by subsequent addition of deionized water or phosphate-buffered saline (PBS) to reach a final concentration of 1 mM. The IFs formed with alkyl segment trapped in the core of the IFs by hydrophobic interactions and the bioactive Z33 sequence displayed in the shell facing towards the solvent (FIG. 2A). After aging overnight at room temperature, transmission electron microscopy (TEM) and circular dichroism (CD) were utilized to characterize the morphology of the assembled nanostructures.

Given the vital role of pH conditions in the current IgG purification method, the self-assembly behavior of C12-Z33 was evaluated in response to pH variations. Neutral pH is normally used as the binding condition, while acidic pH is used to elute antibodies from the protein A affinity column. To study the self-assembly behavior at neutral and low pH, PBS (pH 7.4) and IgG elution buffer (pH 2.8) were utilized as the aqueous environment for the self-assembly of C12-Z33. The morphologies of C12-Z33 IFs at different pH were studied by TEM (FIG. 2C through 2F) and CD (FIG. 2B). It was found that the C12-Z33 molecule could be well-dissolved and self-assemble into nanofibers in both the pH conditions mentioned above. Representative TEM images from a solution of 100 μM C12-Z33 revealed that C12-Z33 self-assembled into nanofibrous structure under both physiological condition and acidic condition with a diameter of 16.0±1.7 nm, a value that is less than the length of the fully extended peptide molecule (about 22.5 nm in β-sheet conformation). The length of the nanofibers was shown in micro-meter scale and could not be well-controlled.

To further understand the molecular packing within the self-assembled structures, circular dichroism (CD) was used to study the peptide secondary structure. Strong negative signals at around 222 nm (n-π*) and 208 nm (π-π*) were observed in C12-Z33, suggesting the formation of α-helix secondary structure of Z33 segment in the self-assembled state as was shown in the pure Z33 peptide. Based on the CD spectra and the measured diameter of IFs, it is rational to infer the peptides maintained their α-helix secondary structure when packing into IFs. It is worth noting that although CD spectra for C12-Z33 in PBS solution or IgG elution buffer only maintained partial α-helix signals, the ellipticity of the two negative peaks at around 222 nm and 208 nm changed compared with Z33 peptide in the same buffer. The shift of the CD spectra may result from the formation of the IFs that can change the molecular packing of Z33 segment from its free state and may subsequently influence its binding affinity to IgG due to the specific conformation required for the binding sites.

Example 3

ITC Experiment for Measuring Binding Affinity of IFs. Given the conformation change in the secondary structure of Z33 peptide after incorporation into IFs, it is of great interest to know if the formation of C12-Z33 IFs would influence the IgG binding ability existing in original Z33 peptide. To investigate the binding affinity of the self-assembled C12-Z33 IFs, thermodynamic properties of the binding to IgG1 were investigated by isothermal titration calorimetry (ITC). ITC has been widely employed to monitor the binding events between great numbers of proteins and ligands, which is an excellent method to explore if the binding could occur between C12-Z33 IFs and IgG1. The heat that is associated with the binding reaction was recorded during the stepwise injections and the thermodynamic parameters including thermodynamic dissociation constant ($K_d$), molar enthalpy change ($\Delta H°$), and stoichiometry (N), can be obtained directly.

TABLE 2

Thermodynamic parameters for binding of Z33-based ligands to IgG1 at 15° C. in phosphate-buffer saline at pH 7.4. Data are reported per ligand.

| Ligands | $K_d$ (nM) | $\Delta G°$ (kcal · mol$^{-1}$) | $\Delta H°$ (kcal · mol$^{-1}$) | $-T\Delta S°$ (kcal · mol$^{-1}$) | N |
|---|---|---|---|---|---|
| Z33 | 60 | -9.5 | -23.1 | 13.6 | 2.31 |
| C12-Z33 | 650 | -8.1 | -9.3 | 1.2 | 3.10 |
| 2C8-Z33 | 1115 | -7.8 | -2.8 | -5.0 | 9.13 |

Thermodynamic parameters for binding of Z33-based ligands to IgG1 at 15° C. in phosphate-buffer saline at pH 7.4. Data are reported per IgG1.

| Ligands | $K_d$ (nM) | $\Delta G°$ (kcal · mol$^{-1}$) | $\Delta H°$ (kcal · mol$^{-1}$) | $-T\Delta S°$ (kcal · mol$^{-1}$) |
|---|---|---|---|---|
| Z33 | 26 | -10.0 | -53.4 | 43.4 |
| C12-Z33 | 209 | -8.8 | -28.9 | 20.1 |
| 2C8-Z33 | 122 | -9.1 | -25.9 | 16.8 |

In a typical ITC experiment, a solution of 100 μM C12-Z33 in PBS buffer was aged overnight and then injected into a solution of 2 μM IgG1 in the same buffer at 15° C., pH 7.4. Typical thermograms and binding isotherms were shown in FIG. 3A and the thermodynamic parameters reported per ligand are summarized in Table 2. The ITC results for the binding of C12-Z33 IFs to IgG1 revealed an enthalpy driven binding event characterized by a $K_d$ of 650. To further compare the binding efficiency of C12-Z33 IFs, we synthesized the Z33 peptide which was proved to bind tightly to IgG1 with a $K_d$ of 43 nM measured by surface plasmon resonance. The binding properties of Z33 peptide to IgG1 was measured by ITC at 15° C. in PBS, pH 7.4 and typical thermograms and binding isotherms were shown in FIG. 3C. In addition to a 100-fold better affinity, the stoichiometry for Z33 was 2.3, whereas the apparent stoichiometry for C12-Z33 was 3.1, indicating that not all the C12-Z33 in IFs were available for the binding to IgG1 molecule. The efficiency of C12-Z33 molecule that is able to bind to IgG1 can be estimated to be 74.2% by dividing the stoichiometry of Z33 by that of C12-Z33.

While normalization per ligand allows the determination of the apparent stoichiometry of binding, comparison of the thermodynamic parameters should be done after normalization per mole of IgG as shown in Table 2. The binding of Z33 to IgG was characterized by a large favorable enthalpy opposed by a large unfavorable entropy change. The thermodynamic signature for the binding of C12-Z33 was similar although the magnitudes of the enthalpy and entropy changes were smaller. Although C12-Z33 binds with a less unfavorable entropy than Z33, the loss in favorable enthalpy is even larger which results in an overall lower binding affinity. An overall loss in the favorable binding enthalpy could possibly be caused by the unfavorable enthalpy associated with the disruption of the IFs. There is also a possibility that favorable interactions with IgG1 are limited due to restrictions in the IFs. Titration of IgG1 with C12-Z33 were also performed in IgG elution buffer (pH 2.8) at 15° C. (FIG. 3B) in order to demonstrate significantly lower binding affinity at this low pH suitable for elution from the IFs.

To exclude the non-specific binding between IFs and IgG1, C12-SZ33 with scrambled Z33 peptide sequence was used as negative control. This C12-SZ33 IAs shows similar self-assembly properties and secondary structures characterized with TEM and CD (data not shown). ITC experiment was carried out by injecting 100 μM C12-SZ33 IAs into 2 μM IgG1 solution at 15° C. in PBS at pH 7.4 to measure their binding ability. The thermograms and binding isotherms in FIG. 3D suggests specific interactions between IgG1 and the Z33 peptide.

Example 4

Figures 7A, 7B, 7C, 7D:
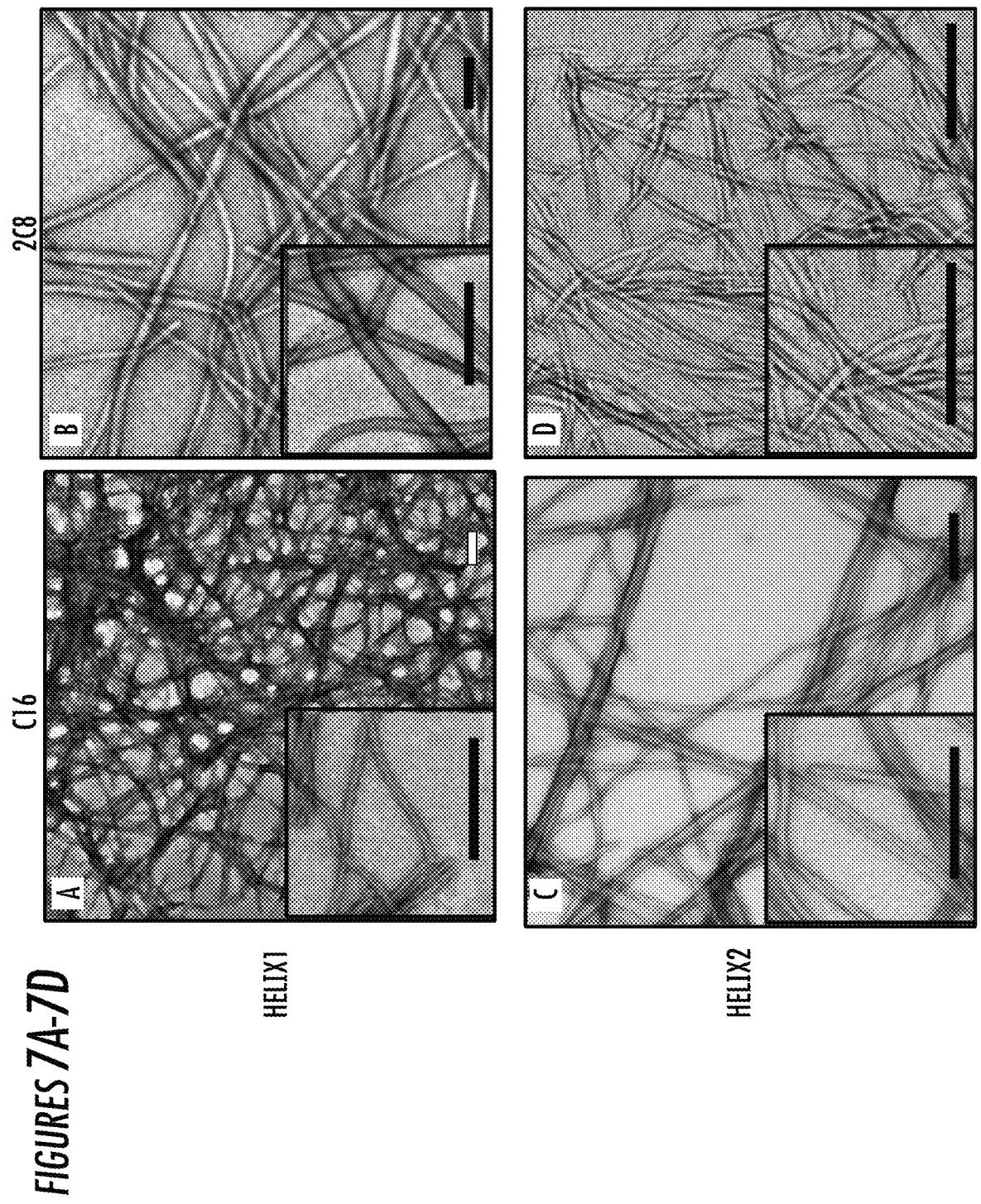
Figures 8A, 8B, 8C, 8D:
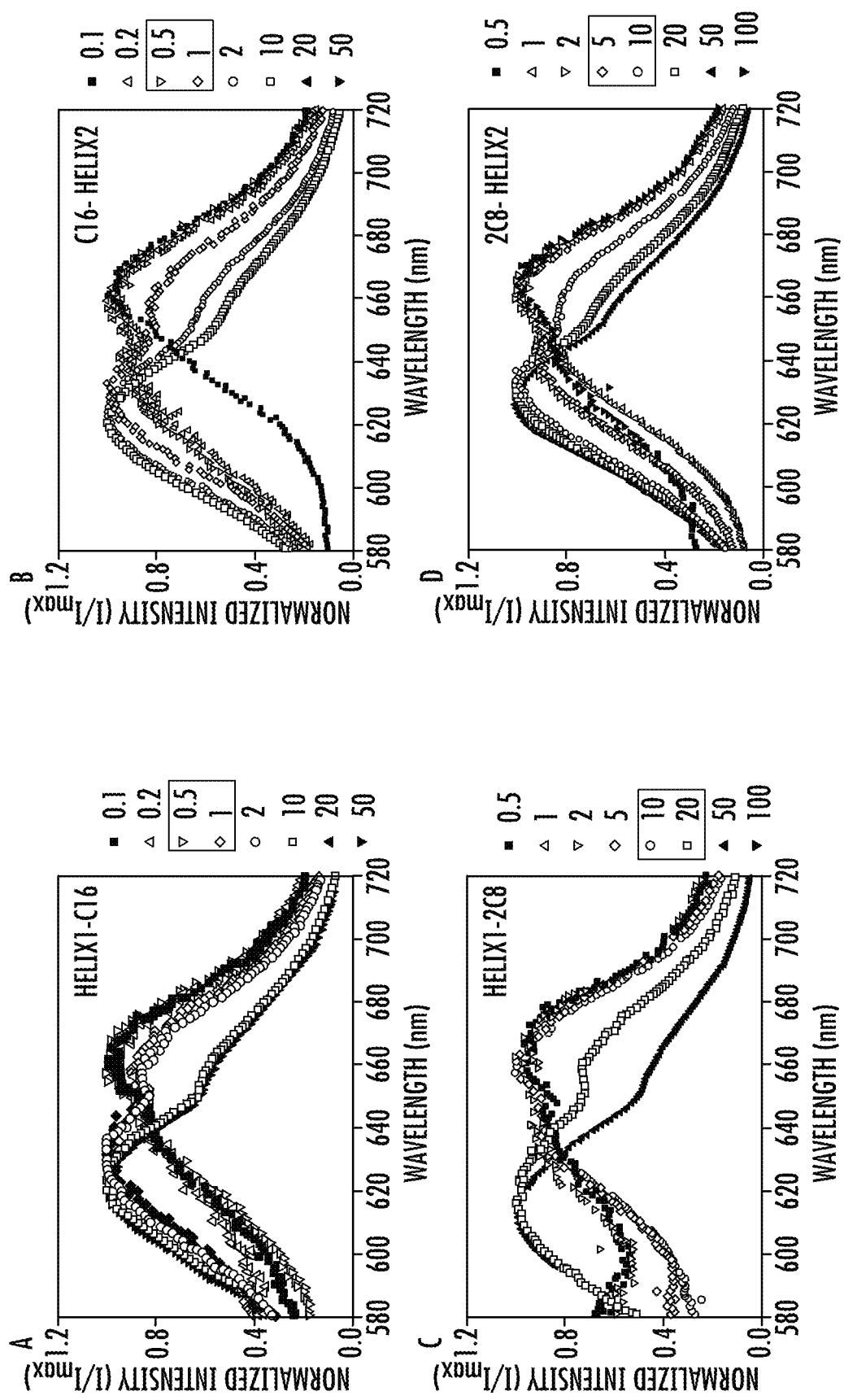

To further prove the universality of the function of IFs, double chain alkylated IAs 2C8-Z33 were also studied from self-assembly property to binding affinity to IgG1 (FIGS. 4A-E). Nanoscale IFs with uniform diameters were observed in TEM image and α-helix secondary structure was confirmed by CD. From the ITC results, binding between 2C8-Z33 and IgG1 occurred at 15° C. in PBS, pH 7.4, whereas no detectable binding occurred in elution buffer, pH 2.8. The apparent stoichiometry for the binding of 2C8-Z33 was 9.1, indicating an even lower efficiency of binding. Although 2C8-Z33 binds with a less favorable enthalpy of binding than C12-Z33, the contribution from the entropy is less unfavorable, which results in binding affinity that is slightly better (Table 2). From the results discussed above, we demonstrated that with the high density of binding sites displayed on the surface, the self-assembled IFs are able to maintain favorable binding ability to IgG1 as was shown in the original Z33 peptide. There is nevertheless a loss in overall binding affinity observed for the IFs, which is of enthalpic origin. The loss in favorable enthalpy can be explained by loss of interactions due to restrictions in the IFs and an unfavorable enthalpy contribution associated with the disruption of the particles. The molecular level packing within IFs determines their morphological as well as functional properties that can greatly affect their performance in bioactivity.

Example 5

Potential Applications for Purification of Immunoglobulin and other Molecules Having an Fc Portion.

The diversity of constituent amino acids provides a broad basis for non-covalent interactions including hydrogen bonding, π-π stacking, hydrophobic collapse, and electrostatic interactions between self-assembling peptide nanofibers. For example, the solubility of acidic and basic amino acids is determined by the degree of ionization, a property that is pH and ionic strength dependent. The self-assembly process of charged peptides can thus be facilitated by tuning the pH or adding salts to reduce the electrostatic repulsions, promote aggregation and even precipitation. Considering the numerous charged amino acid residues displayed in Z33 peptide, a fascinating advantage of our immunofiber system relies in the easily-tunable solubility. Once the IgG is bound to IFs, the IgG-IFs complexes are of high potential to be precipitated out by adding salts with high ionic intensity (FIG. 5A).

C12-Z33 IFs were chosen to study the possibility to precipitate IgG1 because of its relatively high binding affinity to IgG1. As shown in FIG. 5B (i-ii), 5 mM C12-Z33 could be well dissolved in PBS solution but precipitated in a PBS solution of 0.6 M $Na_2SO_4$. The zeta potential of C12-Z33 in PBS solution is −7.61 mV and the addition of $Na_2SO_4$ could screen the charges on the surface of IFs and thus induce precipitation. For IgG1, it is well dissolved in 5 mM C12-Z33 as well as 0.6 M $Na_2SO_4$. However, precipitation was observed after mixing 20 μM IgG1 and 5 mM C12-Z33 for 5 minutes followed by addition of 0.6 M $Na_2SO_4$. To determine composition of the precipitates, two parallel experiments were carried out. 5 mM C12-Z33 in 0.6 M $Na_2SO_4$ was centrifuged and ultraviolet-visible (UV-Vis) spectroscopy was used to monitor the absorbance changes of supernates at 280 nm before and after the addition of $Na_2SO_4$. Same procedures were conducted on a mixture of 5 mM C12-Z33 and 20 μM IgG1 in 0.6 M $Na_2SO_4$. As is shown in FIG. 5C, most C12-Z33 IFs were able to be precipitated out by 0.6 M $Na_2SO_4$. For IgG1-IF complex system, the absorbance at 280 nm was reduced to a level below the initial absorbance of IgG1, indicating the removal of IgG1 from the solution. More clearly, the absorbance of supernate of net IgG1 was plotted via subtracting the value of green line from the blue line, suggesting more than 60% IgG1 was removed from the supernate. So far, the possibility of our IFs to serve as a new affinity precipitation agent was preliminary proved.

Example 6

Molecular Design of IAs with Fragmented Antibody Binding Peptides. The peptide sequence of Z33 (FNMQQQRRFYEALHDPNLNEEQRNAKIKSIRDD) (SEQ ID NO: 1) containing two α-helices was separated between D and P and alkylated into two series of immuno-amphiphiles: 1) Helix1 (FNMQQQRRFYEALHD) (SEQ ID NO: 2)-based immuno-amphiphiles; 2) Helix2 (PNLNEEQRNAKIKSIRDD) (SEQ ID NO: 5) -based immuno-amphiphiles. We were interested in the possible conformation changes in peptide structures after separation, alkylation and self-assembly. C16 and 2C8 alkyl chains were conjugated on to the C-terminus of Helix1 and N-terminus of Helix2 (FIG. 6A). The reason we conjugated alkyl tails on the different terminus of the Helix1 and Helix2 peptides was to maintain the relative position between helices and other segment as shown in the Z33 peptide. The IAs were supposed to associate under certain conditions with alkyl segment trapped in the hydrophobic core and the peptide sequence facing towards the aqueous environment (FIG. 6B). All the molecules were synthesized and purified using automated solid-phase peptide synthesis (SPPS) methods and RP-HPLC. The purity and expected molecular masses of the synthesized compounds were confirmed using analytical HPLC and mass spectrometry.

Example 7

Molecular Assembly of IAs with Fragmented Antibody Binding Peptides. The self-assembly of IAs was achieved through a two-step operation. The IAs were first pretreated with HFIP to eliminate any pre-existing nanostructures formed during the synthesis and purification process. HFIP were then removed via evaporation, followed by subsequent addition of deionized water to reach a final concentration of 1 mM at pH 7.4 and age overnight. To investigate how alkylation can impact morphology of self-assembled IAs, TEM were utilized for all the IAs to visualize the assembled morphologies and representative TEM images of 100 μM IA solutions are shown in FIG. 7. FIGS. 7A and 7C reveal that both Helix1-C16 and C16-Helix2 self-assembled into long nanofibrous structures with a diameter of 9.6±1.3 nm and 12.4±1.7 nm, respectively. Two or more nanofibers were also observed to merge together into nanobelts due to the charge screening. The length of the nanofibers was shown in micro-meter scale and could not be well-controlled. For double-chain alkylation with octonoic acid (C8), filamentous assemblies were also found for both Helix1-2C8 and 2C8-Helix2 under the same conditions (FIGS. 7B and 7D). However, these filaments are relatively shorter, also appearing more polydisperse in length. In addition, variations in the diameter were observed, with smallest filaments possessing a diameter of 11.0±1.4 nm for Helix1-2C8 filaments and of 9.3±1.3 nm for Helix2-2C8 filaments. We assume that the steric effect of the large double-chain may play a vital role in the morphology of assemblies. However, the impact of the steric effect on different peptide amphiphile systems varies. Stupp and coworkers found that increasing the steric effect in the end group of alkyl chains tends to reduce the superhelical pitch. In a Tat peptide-based nanofiber system, only quart-C8 conjugates can self-assemble into filamentous nanostructures, and no nanostructures were observed for either di-C8 or mono-C8 conjugates.

Example 8

To deeply understand the differences between single-chain and double-chain alkylated IAs with fragmented antibody binding peptides, further studies on CMC and secondary structures were conducted. The critical micelle concentration (CMC) values for various IAs were measured using Nile Red, a lipophilic dye that fluoresces depending on solvent polarity. Intensive fluorescence upon exposure to hydrophobic environments can be strongly quenched and red-shifted in aqueous media. When incubated with IAs at different concentrations in aqueous solution, Nile Red prefers to partition into the hydrophobic core offered by the self-assembled nanostructures and the CMC of IAs was determined when a blue-shift of the emission maximum occurred. FIG. 8A shows a plot of concentration of Helix1-C16 versus Nile Red fluorescence intensity. The emission maximum wavelength was dominated at 660 nm until 0.5 μM, then a blue-shift from 660 nm to 635 nm first occurs at the concentration of 1 μM, suggesting a CMC value in between. Similarly, CMC values for C16-Helix2, Helix1-2C8, and 2C8-Helix2 can be obtained from FIG. 8B-8D. Double-chain alkylation exhibit higher CMC values compared to the single-chain alkylation. 2C8-Helix2 shows a stronger tendency for aggregation than Helix1-2C8, since the former have lower ranges of CMC values.

Example 9

Secondary Structure Investigation of Alkylated IAs with Fragmented Antibody Binding Peptides.

To understand the molecular packing within the self-assembled structures, circular dichroism (CD) was used to study the peptide secondary structure. As shown in FIG. 9, both Helix1 and Helix2 lost the α-helical structures and displayed random coil CD spectra after being isolated from Z33 (FIG. 16), which may result from the destruction of mutual dependence for stability. Helix1-C16 and C16-Helix2 assemblies exhibit strong negative signals at around 218 nm (n-π* transition), suggesting the formation of β-sheet secondary structures in both IAs. The β-sheet conformation has previously been proven to play an important role in promoting the formation of well-defined one-dimensional nanostructures. Interestingly, negative signals at around 225 nm (n-π* transition) and 208 nm (π-π* transition) were observed in Helix1-2C8 and 2C8-Helix2, indicating the presence of α-helix secondary structure. The resulting CD spectra were fit using a linear combination of polylysine basis spectra to evaluate the content of each secondary structures (FIG. 17). β-sheet are major constituent of Helix1-C16 and C16-Helix2 IAs, while double-chain alkylated IAs present α-helix dominated secondary structures.

Example 10

To further confirm the component of secondary structures in the self-assembled IAs, a fluorescent dye Thioflavin-T (ThT) with large enhancement of its fluorescence emission upon binding to β-sheet surfaces was used to examine the existence of β-sheet secondary structures in Helix1-based IAs. As shown in FIG. 18, ThT emissions of pre-incubated Helix1 and Helix1-2C8 at 482 nm maintain a similar or slightly increased level compared with that of the pure ThT solution, implying no prominent β-sheet existing in those IAs. In the contrary, a dramatic increase of fluorescence was observed in both pre-incubated Helix1-C16, which corresponds to the dominant β-sheet secondary structures examined by CD.

One may argue that the CD signals may come from the free monomers instead of the self-assembling filaments. To exclude this possibility, CD spectra of diluted solutions of α-helix IA (represented by Helix1-2C8) and β-sheet IA (represented by Helix1-C16) were taken. FIGS. 10A and 10B show that CD signals become prominent and stable only when the IA concentration surpassed corresponding CMC value, revealing that the packing of the IAs in the filamentous structures is the major contributor to the CD signals.

As known from the geometry of α-helix and β-sheet, the interhelical axis distance is around 12 Å, while β-strands are spaced by 5 Å, indicating a closer packing is needed for the formation of β-sheet than α-helix. It has been proven that longer alkyl chains tend to pack tighter and even crystalize in the self-assembled nanostructures, which can bring the peptide segments into closer proximity. For 2C8 conjugation, it should be noticed that two C8 chains were conjugated onto the Helix1 and Helix2 in an asymmetric way. Two C8 were conjugated on two adjacent lysine at the C-terminal of Helix1, and for Helix2 one was conjugated on the N-terminal amine and the other on the side chain of lysine. Increasing the number of alkyl chains with asymmetric structures can largely increase the steric hindrance and attenuate aggregation, resulting in relatively large CMC, loose packing, and wider diameter of filaments.

Example 11

Effect of Single Alkyl Chain Length.

Since the looser packing of double-chain alkylated IAs promote the formation and stabilization of α-helix assemblies, we assume that shortening the length of single alkylated chains may have same effect. In order to confirm this assumption, two shorter alkyl chains (lauric acid, C12; octanoic acid, C8) were conjugated on to Helix1 and Helix2 separately and the assemblies were characterized with TEM and CD. No well-defined nanostructures and emission maximum transitions were observed for either Helix1-C8 or C8-Helix2 at the highest tested concentration of 100 μM, indicating these two IAs cannot self-assemble below this concentration. Helix1-C12 and C12-Helix2 (FIGS. 11A and 11B) associated into long nanofibers with a diameter of 12.2±1.4 nm and 9.1±1.6 nm, respectively. It should be noted that the diameter of the nanofibers not only relates to the length of the chemical structures but also the packing state. Therefore, it's not surprising that we observed smaller diameters in the C16 conjugated IAs with lower CMC values (FIGS. 11C and 11D) and tighter packing than C12 conjugates due to the stronger hydrophobic interactions. In CD spectra (FIGS. 11E and 11F), both Helix1-C8 and C8-Helix2 show similar CD results as the unconjugated peptides do due to their low ability to aggregate. Interestingly, β-sheet signal appears in the CD spectrum of Helix1-C12, nevertheless, α-helix secondary structure was observed in C12-Helix2, which confirmed our previous assumption. For single-chain alkylation, self-assembled IAs with longer alkyl chains can induce the tight packing between adjacent IA molecules and promote the formation of β-sheet, while the looser packing in the shorter chain alkylated IAs can provide more spaces for the α-helix structures.

designed for further separating antibody binding peptide (Z33) from the alkyl chains. When dissolving the binding and spacer molecules in aqueous solution, these two molecules can homogeneously co-assemble into one-dimensional immunofibers with the binding ligand Z33 sticking out on the surface (FIG. 19B). The distance of two Z33 ligands can be controlled by tuning the molar ratio of the binding and spacer molecules for co-assembly. Representative TEM images of self-assembled C12-VVEE (SEQ ID NO: 10) (FIG. 20A) and C12-VVEE (SEQ ID NO: 10) (FIG. 20B) show cylindrical nanofiber structures in PBS, pH 7.4. FIG. 20C shows co-assembled nanofibers at 10:1 molar ratio of C12-VVEE (SEQ ID NO: 10) and C12-VVKKGG(SEQ ID NO: 9) -Z33.

Example 13

To investigate the IgG binding and precipitation ability with the new immunofibers binding system, 100 µl of

TABLE 3

Summary of IAs with fragmented antibody binding peptides

| Abbreviation | IAs | Main Secondary Structure (100 µM) | CMC (µM) |
|---|---|---|---|
| Helix1-C8 | FNMQQQRRFYEALHDK (SEQ ID NO: 3)-$C_8H_{15}O$ | Random coil | >100 |
| Helix1-C12 | FNMQQQRRFYEALHDK(SEQ ID NO: 3)-$C_{12}H_{21}O$ | β-sheet | 5-10 |
| Helix1-C16 | FNMQQQRRFYEALHDK(SEQ ID NO: 3)-$C_{16}H_{31}O$ | β-sheet | 0.5-1 |
| Helix1-2C8 | FNMQQQRRFYEALHDKK(SEQ ID NO: 4)-$(C_8H_{15}O)2$ | α-helix | 10-20 |
| C8-Helix2 | $C_8H_{15}O$- PNLNEEQRNAKIKSIRDD (SEQ ID NO: 5) | Random coil | >100 |
| C12-Helix2 | $C_{12}H_{21}O$- PNLNEEQRNAKIKSIRDD (SEQ ID NO: 5) | α-helix | 2-5 |
| C16-Helix2 | $C_{16}H_{31}O$- PNLNEEQRNAKIKSIRDD (SEQ ID NO: 5) | β-sheet | 0.5-1 |
| 2C8-Helix2 | $(C_8H_{15}O)2$-KPNLNEEQRNAKIKSIRDD (SEQ ID NO: 7) | α-helix | 5-10 |

Example 12

Preparation of Alternative Immunofiber Compositions Comprising an Immunofiber Binding Composition and an Immunofibers Spacer Composition.

As described above, an improved immunofibers based binding system was designed by combining binding immunofibers molecules (C12-VVKKGG (SEQ ID NO: 9) -Z33) and spacer molecules (C12-VVEE, SEQ ID NO: 10) in a co-assembled immunofiber system (FIG. 19A). The binding molecule contains 6 more amino acids residues VVKKGG (SEQ ID NO: 9) between the carbon chain and binding peptide Z33 than the original design C12-Z33. Two valines (VV) promotes the formation of one-dimensional structures. Two glutamine acids (EE) were designed as the hydrophilic segment in the spacer molecule and two lysine (KK) were designed accordingly for electrostatic interactions between KK and EE, and thus, inducing the alternating packing of binding and spacer molecules. Two glycine (GG) were desired immunofibers solution was incubated with IgG (with a 10:1 molar ratio of C12-VVKKGG(SEQ ID NO: 9) -Z33 and IgG) for half an hour followed by adding ammonium sulfate to a final concentration of 1 M to trigger the precipitation of the immunofibers and IgG. When mixing self-assembled C12-VVKKGG (SEQ ID NO: 9) -Z33 and IgG, no precipitation was observed after the addition of ammonium sulfate. Interestingly, the solution containing IgG and co-assembled C12-VVEE (SEQ ID NO: 10) and C12-VVKKGG (SEQ ID NO: 9) -Z33 at a molar ratio of 10:1 became cloudy after adding salts. After centrifuging down the precipitates and analyzing the IgG concentration in the supernatant, about 30% IgG were precipitated out from the solution. IgG concentration was quantified with a ProA column (TSKgel® Protein A-5PW, 20 μm, 35×4.6 mm) monitored at 280 nm. This preliminary result showed that with a same amount of binding molecule and IgG in the solution, the addition of spacer molecule plays an important role in the IgG capture and precipitation. Spacing the binding molecule and sticking out the binding ligand Z33 at the surface of immunofibers provides more ligand flexibility and IgG accessibility.

Example 14

To increase the IgG binding efficiency and optimal precipitation condition in the co-assembled immunofibers binding system, several factors will continue to be optimized including the ratio of binding molecules to spacer molecules, the ratio of binding molecules to IgG, salt concentration, binding and salting time, and so on. The molar ratio of C12-VVEE (SEQ ID NO: 10) and C12-VVKKGG(SEQ ID NO: 9) -Z33 and the molar ratio of C12-VVKKGG(SEQ ID NO: 9) -Z33 were firstly studied and preliminary results were shown in FIG. 21. At a 10:2 molar ratio of C12VVKKGG(SEQ ID NO: 9) -Z33 to IgG and 1 M ammonium sulfate, 5 molar ratios of C12-VVEE (SEQ ID NO: 10) to C12-VVKKGG(SEQ ID NO: 9) -Z33 (5:1, 10:1, 25:1, 50:1, 100:1) were tested. FIG. 21A shows the IgG percentages in the supernatant after salting out and centrifugation. With the increase of the content of C12-VVEE (SEQ ID NO: 10), more IgG precipitated out from the solution and reached the highest yield about 75% at 50:1. It should be noted that the decrease of the precipitation yield at 100:1 may results from the lower solubility of the immunofibers due to the high concentration. The molar ratio of C12-VVKKGG(SEQ ID NO: 9) -Z33 to IgG was then tuned from 10:4, 10:2, to 10:1 using the 25:1 and 50:1 immunofiber systems which showed better performance in FIG. 3B. As shown in FIG. 3B, these two immunofibers systems followed the same trend that the yield of IgG precipitation increased as the increase of the ratio of C12-VVKKGG(SEQ ID NO: 9) -Z33 to IgG. At the best condition, a 99% IgG precipitation yield could be reached in the 50:1 immunofiber system at 10:1 ratio of C12-VVKKGG(SEQ ID NO: 9) -Z33 to IgG. This exciting result confirms that the co-assembled immunofibers possess high IgG binding and precipitation ability. More systematic studies will be conducted on the optimization of conditions for IgG precipitation and recovery.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

SEQUENCE LISTING

```
Sequence total quantity: 10
SEQ ID NO: 1            moltype = AA  length = 33
FEATURE                 Location/Qualifiers
REGION                  1..33
                        note = synthetic sequence
source                  1..33
                        mol_type = protein
                        organism = synthetic construct
SEQUENCE: 1
FNMQQQRRFY EALHDPNLNE EQRNAKIKSI RDD                              33

SEQ ID NO: 2            moltype = AA  length = 15
FEATURE                 Location/Qualifiers
REGION                  1..15
                        note = synthetic sequence
source                  1..15
                        mol_type = protein
                        organism = synthetic construct
SEQUENCE: 2
FNMQQQRRFY EALHD                                                  15

SEQ ID NO: 3            moltype = AA  length = 16
FEATURE                 Location/Qualifiers
REGION                  1..16
                        note = synthetic sequence
```

```
source                   1..16
                         mol_type = protein
                         organism = synthetic construct
SEQUENCE: 3
FNMQQQRRFY EALHDK                                                    16

SEQ ID NO: 4             moltype = AA  length = 17
FEATURE                  Location/Qualifiers
REGION                   1..17
                         note = synthetic sequence
source                   1..17
                         mol_type = protein
                         organism = synthetic construct
SEQUENCE: 4
FNMQQQRRFY EALHDKK                                                   17

SEQ ID NO: 5             moltype = AA  length = 18
FEATURE                  Location/Qualifiers
REGION                   1..18
                         note = synthetic sequence
source                   1..18
                         mol_type = protein
                         organism = synthetic construct
SEQUENCE: 5
PNLNEEQRNA KIKSIRDD                                                  18

SEQ ID NO: 6             moltype = AA  length = 19
FEATURE                  Location/Qualifiers
REGION                   1..19
                         note = synthetic sequence
source                   1..19
                         mol_type = protein
                         organism = synthetic construct
SEQUENCE: 6
FPNLNEEQRN AKIKSIRDD                                                 19

SEQ ID NO: 7             moltype = AA  length = 19
FEATURE                  Location/Qualifiers
REGION                   1..19
                         note = synthetic sequence
source                   1..19
                         mol_type = protein
                         organism = synthetic construct
SEQUENCE: 7
KPNLNEEQRN AKIKSIRDD                                                 19

SEQ ID NO: 8             moltype = AA  length = 8
FEATURE                  Location/Qualifiers
REGION                   1..8
                         note = synthetic sequence
source                   1..8
                         mol_type = protein
                         organism = synthetic construct
SEQUENCE: 8
GANPNAAG                                                             8

SEQ ID NO: 9             moltype = AA  length = 6
FEATURE                  Location/Qualifiers
REGION                   1..6
                         note = synthetic sequence
source                   1..6
                         mol_type = protein
                         organism = synthetic construct
SEQUENCE: 9
VVKKGG                                                               6

SEQ ID NO: 10            moltype = AA  length = 4
FEATURE                  Location/Qualifiers
REGION                   1..4
                         note = synthetic sequence
source                   1..4
                         mol_type = protein
                         organism = synthetic construct
SEQUENCE: 10
VVEE                                                                 4
```

The invention claimed is:

1. An immunofiber composition comprising:

a) a spacer molecule having a hydrocarbon chain at its N-terminus conjugated to a peptide sequence comprising the generic amino acid sequence of XXBB, wherein XX is two amino acids having a small hydrophobic side chain and can be the same or different amino acid, and wherein BB is two amino acids having a negatively charged side chain and can be the same or different amino acid; and b) an immunofiber binding molecule comprising an antibody binding peptide conjugated to a second hydrocarbon chain, wherein the antibody binding peptide has a hydrophilic amino acid sequence selected from the group consisting of SEQ ID NOS: 1-7.

2. The immunofiber composition of claim 1, wherein each of the amino acids having a small hydrophobic side chain is independently selected from the group consisting of: Ala, Val, Ile, and Leu.

3. The immunofiber composition of claim 1, wherein each of the amino acids having a negatively charged side chain is independently selected from the group consisting of: Glu and Asp.

4. The immunofiber composition of claim 1, wherein XXBB is VVEE (SEQ ID NO: 10).

5. The immunofiber composition of claim 1, wherein the hydrocarbon chain is a C12 hydrocarbon chain.

6. The immunofiber composition of claim 1, wherein the antibody binding peptide has the amino acid sequence FNMQQQRRFYEALHDPNLNEEQRNAKIKSIRDD (SEQ ID NO: 1).

7. The immunofiber composition of claim 1, wherein the second hydrocarbon chain is between 8 and 22 carbons in length and is either linear or branched.

8. The immunofiber composition of claim 1, wherein the second hydrocarbon chain is between 8 and 12 carbons in length.

9. A method for purifying antibodies or Fc-containing peptides or proteins, said method comprising:

a) dissolving the immunofiber composition of claim 1 in an aqueous solution at a physiological pH to provide an immunofiber solution and aging the immunofiber solution overnight to provide a solution of self-assembled immunofibers;

b) mixing a sample comprising antibodies or Fc-containing peptides or proteins with the solution of self-assembled immunofibers to provide a solution comprising immunofiber/antibody complexes or immunofiber/Fc-containing peptide or protein complexes;

c) separating the immunofiber/antibody complexes or the immunofiber/Fc-containing peptide or protein complexes from the solution by adding salt and centrifuging; and d) dissociating the immunofibers from the antibodies or Fc-containing peptide or protein complexes and collecting the unbound antibodies or Fc-containing peptides or proteins.

10. The method of claim 9, wherein aging the immunofiber solution overnight promotes binding of the immunofibers to the Fc portions of the antibodies or Fc-containing peptides or proteins.

11. The method of claim 9, wherein dissociating the immunofibers from the antibodies or Fc-containing peptides or proteins comprises lowering the pH to an elution condition; and using one or more of filtration, microfiltration, or ultrafiltration.

12. The method of claim 9, further comprising further purifying the antibodies or Fc-containing peptides or proteins using polishing.

* * * * *